US011988650B2

(12) United States Patent
Cong et al.

(10) Patent No.: US 11,988,650 B2
(45) Date of Patent: May 21, 2024

(54) DETERMINATION OF THE AMORPHOUS CONTENT OF POLYMERS

(71) Applicant: Dow Global Technologies LLC, Midland, MI (US)

(72) Inventors: Rongjuan Cong, Lake Jackson, TX (US); Kimberly L. Bailey, Pearland, TX (US); Vickie Ricca, Lake Jackson, TX (US)

(73) Assignee: Dow Global Technologies LLC, Midland, MI (US)

( * ) Notice: Subject to any disclaimer, the term of this patent is extended or adjusted under 35 U.S.C. 154(b) by 670 days.

(21) Appl. No.: 17/256,994

(22) PCT Filed: Jun. 25, 2019

(86) PCT No.: PCT/US2019/039003
§ 371 (c)(1),
(2) Date: Dec. 29, 2020

(87) PCT Pub. No.: WO2020/005953
PCT Pub. Date: Jan. 2, 2020

(65) Prior Publication Data
US 2021/0132011 A1    May 6, 2021

Related U.S. Application Data

(60) Provisional application No. 62/691,733, filed on Jun. 29, 2018.

(51) Int. Cl.
*G01N 30/54*  (2006.01)
*G01N 30/00*  (2006.01)
(Continued)

(52) U.S. Cl.
CPC ......... *G01N 30/54* (2013.01); *G01N 30/8679* (2013.01); *G01N 33/442* (2013.01); *G01N 2030/008* (2013.01); *G01N 2030/885* (2013.01)

(58) Field of Classification Search
CPC .... G01N 30/54; G01N 30/8679; G01N 30/30; G01N 2030/008; G01N 2030/885; G01N 2030/027; G01N 33/442; B01D 9/003
See application file for complete search history.

(56) References Cited

U.S. PATENT DOCUMENTS 3,205,290 A * 9/1965 Covington, Jr. ....... B29D 23/00
264/234
8,802,772 B2  8/2014 El-Hibri et al.
2018/0172648 A1  6/2018 Cong et al.

FOREIGN PATENT DOCUMENTS

JP  2015163461 A1  9/2015
WO  2017040127 A1  3/2017
(Continued)

OTHER PUBLICATIONS

Abhishek et al., Macromolecules, American Chemical Society, 2010. p. 3710-3720, vol. 43, No. 8.
Liu Weifeng et al., European Polymer Journal, 2014, p. 160-171, vol. 34.
Monrabal et al., Macromolecular Symposia, 2007, p. 71-79, vol. 257, No. 1.
(Continued)

*Primary Examiner* — Manuel L Barbee

(57) ABSTRACT

A method to determine the weight percent of an "amorphous" fraction in an olefin-based polymer composition, comprising one or more olefin-based polymers; said method comprising the following steps: a) dissolving the olefin-based polymer composition in an organic solvent to form a polymer solution; b) injecting at least a portion of the polymer solution onto a support material, and wherein the support material has a Co-crystallization Index (CI) value from 0.70 to 1.20; c) cooling the support material at a rate greater than, or equal to, 0.2 C/min; d) increasing the
(Continued)

temperature of the support material to elute the polymers of the olefin-based polymer composition; e) generating a chromatogram; f) determining the peak area of the first elution from its lower integration limit to its upper integration limit; g) calculating the "amorphous" fraction" based on the following Equation A below: wt % "amorphous" fraction=$PA_{amorphous}/PA_{total}\times 100$ (Eqn. A); wherein $PA_{amorp}$=peak area of the first elution, and PAtotal #191=total peak area of the polymers of the olefin-based polymer composition.

12 Claims, 3 Drawing Sheets

(51) Int. Cl.
　　*G01N 30/86*　　(2006.01)
　　*G01N 33/44*　　(2006.01)
　　*G01N 30/88*　　(2006.01)

(56) References Cited

FOREIGN PATENT DOCUMENTS

| WO | 2020000337 A1 | 1/2020 |
| WO | 2020000338 A1 | 1/2020 |
| WO | 2020000339 A1 | 1/2020 |

OTHER PUBLICATIONS

Monrabel et al., Advances in Polymer Science, 2013, p. 203-252, vol. 257.
PCT/US2019/039003, International Preliminary Report on Patentability with a mailing date of Dec. 29, 2020.
PCT/US2019/039003, International Search Report and Written Opinion with a mailing date of Oct. 17, 2019.
Stoclet et al., Polymer, 2015, p. 165-175, vol. 72.
Wild et al., Journal of Polymer Science Part B: Polymer Physics, 1982, p. 441-455, vol. 20.

\* cited by examiner

DETERMINATION OF THE AMORPHOUS CONTENT OF POLYMERS

BACKGROUND

Xylene Soluble (XS) is an important property for propylene based polymers, widely used to control polypropylene properties. It is related to the atactic, amorphous polymer fraction in polypropylene. The XS is also used to represent the amount of amorphous material in an impact copolymer. The Xylene Soluble weight fraction (or XS %) of an olefin block composite is used to quantify block composite index (BCI) (see, for example, U.S. Pat. No. 8,802,772).

The percent Xylene Soluble (XS %) can be measured by ASTM D 5492-17, through a procedure with several steps. A Flow Injection Polymer Analysis (FIPA) was developed to generate an equivalent XS %; however, for materials with high XS % values and/or with amorphous fractions having a high molecular weight obtaining a reliable XS % for these cases can be challenging due to difficult filtrations.

This is a need for an accurate and fast method to measure the amorphous fraction in a polymer sample, and which can be used to obtain equivalent, or close, values to those obtained by ASTM 5492-17. This need is fulfilled by the following invention.

SUMMARY OF THE INVENTION

A method to determine the weight percent of an "amorphous" fraction in an olefin-based polymer composition, comprising one or more olefin-based polymers; said method comprising the following steps:
a) dissolving the olefin-based polymer composition in an organic solvent to form a polymer solution;
b) injecting at least a portion of the polymer solution onto a support material, and wherein the support material has a Co-crystallization Index (CI) value from 0.70 to 1.20;
c) cooling the support material at a rate greater than, or equal to, 0.2° C./min;
d) increasing the temperature of the support material to elute the polymers of the olefin-based polymer composition;
e) generating a chromatogram;
f) determining the peak area of the first elution from its lower integration limit to its upper integration limit;
g) calculating the "amorphous" fraction" based on the following Equation A below:

$$\text{wt \%"amorphous" fraction} = PA_{amorp}/PA_{total} \times 100 \quad \text{(Eqn. A);}$$

wherein $PA_{amorp}$=peak area of the first elution, and $PA_{total}$=total peak area of the polymers of the olefin-based polymer composition.

DETAILED DESCRIPTION

Figure 1:
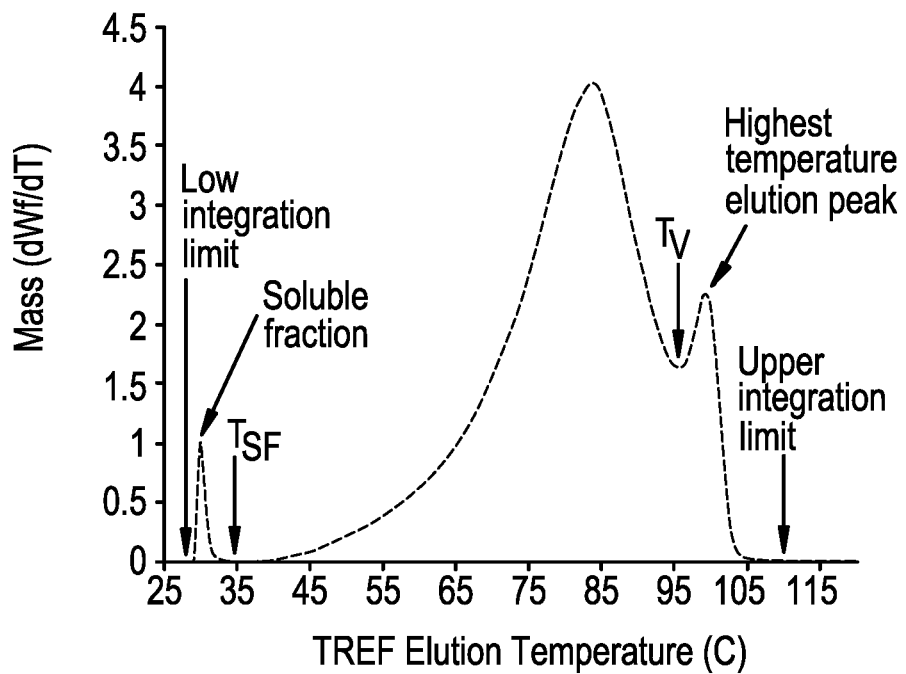
FIG. 1 is a TREF chromatogram of DOWLEX 2056A, which is noted for the calculation of $A_f$. See the discussion of the Co-crystallization Index below.

A new "crystallization based chromatography" method has been discovered to accurately determine the amount of amorphous fraction in an olefin-based polymer composition. This method provides very close, or equivalent, results to those obtained by ASTM 5497-17. Moreover, the inventive method require a fraction of the time (for example, less than 18%) of the analysis time needed for ASTM D5497-17. Moreover, the new method can be fully automated.

As discussed above, a method is provided to determine the weight percent of an "amorphous" fraction in a olefin-based polymer composition, comprising one or more olefin-based polymers; said method comprising the following steps:
a) dissolving the olefin-based polymer composition in an organic solvent (for example, dichlorobenzene or trichlorobenzene) to form a polymer solution;
b) injecting at least a portion of the polymer solution onto a support material, and wherein the support material has a Co-crystallization Index (CI) value from 0.70 to 1.20;
c) cooling the support material at a rate greater than, or equal to, 0.2° C./min;
d) increasing the temperature of the support material to elute the polymers of the olefin-based polymer composition;
e) generating a chromatogram (for example, concentration (Intensity) versus temperature);
f) determining the peak area of the first elution from its lower integration limit to its upper integration limit;
g) calculating the "amorphous" fraction" based on the following Equation A below:

$$\text{wt \%"amorphous" fraction} = PA_{amorp}/PA_{total} \times 100 \quad \text{(Eqn. A);}$$

wherein $PA_{amorp}$=peak area of the first elution, and $PA_{total}$=total peak area of the polymers of the olefin-based polymer composition.

An inventive method may comprise a combination of two or more embodiments as described herein.

The olefin-based polymer composition may comprise a combination of two or more embodiments as described herein.

In one embodiment, or a combination of embodiments described herein, the first elution has a lower integration limit from 10° C. to 15° C.

In one embodiment, or a combination of embodiments described herein, the first elution has an upper integration limit from 30° C. to 45° C., or from 30° C. to 40° C.

In one embodiment, or a combination of embodiments described herein, the first elution is integrated from 10° C. to 40° C., or from 12° C. to 40° C., or from 15° C. to 40° C.

In one embodiment, or a combination of embodiments described herein, the olefin-based polymer composition comprises two olefin-based polymers.

In one embodiment, or a combination of embodiments described herein, the olefin-based polymer composition comprises three olefin-based polymers.

In one embodiment, or a combination of embodiments described herein, the olefin-based polymer composition comprises from 2 to 3 olefin-based polymers.

In one embodiment, or a combination of embodiments described herein, the olefin-based polymer composition comprises a majority amount of polymerized ethylene, based on the weight of the olefin-based polymer composition.

In one embodiment, or a combination of embodiments described herein, the olefin-based polymer composition comprises a majority amount of polymerized propylene, based on the weight of the olefin-based polymer composition.

In one embodiment, or a combination of embodiments described herein, the olefin-based polymer composition is a "block composite" ("BC") that comprises the following three polymer components:
(i) an ethylene-based polymer (EP) having an ethylene content from 10 mol % to less than 90 mol % (a soft copolymer), based on the total moles of polymerized monomer units in the ethylene-based polymer (EP);
(ii) an alpha-olefin-based polymer (AOP) having an alpha-olefin content of greater than 90 mol % (a hard copolymer), based on the total moles of polymerized monomer units in the alpha-olefin-based polymer (AOP); and
(iii) a block copolymer having an ethylene block (EB) and an alpha-olefin block (AOB); wherein the ethylene block (soft block/soft segment) contains more polymerized ethylene than the alpha-olefin block (hard block/hard segment), and
wherein the ethylene block has the same or similar Tm as the ethylene-based polymer (EP) of component (i), and
wherein the alpha-olefin block has the same or similar Tm as the alpha-olefin-based polymer (AOP) of component (ii); and
wherein the phrase "same or similar" refers to an absolute Tm differential of ≤5° C., further ≤4° C., further ≤3° C., further ≤2° C.

In one embodiment, or a combination of embodiments described herein, the olefin-based polymer composition is a "crystalline block composite" ("CBC") that comprises the following three polymer components:
(i) a crystalline ethylene based polymer (CEP) having an ethylene content of greater than, or equal to, 90 mol % (also referred to herein as a soft polymer of CBC), based on the total moles of polymerized monomer units in the crystalline ethylene-based polymer (CEP);
(ii) a crystalline alpha-olefin based polymer (CAOP) having an alpha-olefin content of greater than 90 mol % (also referred to herein as a hard polymer of the CBC), based on the total moles of polymerized monomer units in the crystalline alpha-olefin-based polymer (CAOP); and
(iii) a block copolymer comprising a crystalline ethylene block (CEB) and a crystalline alpha-olefin block (CAOB); and
wherein the crystalline ethylene block has the same or similar Tm as the crystalline ethylene-based polymer (CEP) of component (i), and
wherein the crystalline alpha-olefin block has the same or similar Tm as the crystalline alpha-olefin-based polymer (CAOP) of component (ii); and
wherein the phrase "same or similar" refers to an absolute Tm differential of ≤5° C., further ≤4° C., further ≤3° C., further ≤2° C.

In one embodiment, or a combination of embodiments described herein, the olefin-based polymer composition has a concentration in the solution ≥0.1 milligrams polymer per milliliter of solution.

In one embodiment, or a combination of embodiments described herein, the inventive method is connected in-line, at-line or on-line to either a polymerization process or an isolation process of a polymer blend or polymer composition.

In one embodiment, or a combination of embodiments described herein, the inventive method is used in a multi-dimensional chromatography system.

An inventive method can be coupled, on or off line, with other analytical methods. For example, the effluent from an SEC column containing a copolymer of a selected molecular size can be analyzed by Temperature Rising Elution Fractionation (TREF), or Crystallization Elution Fractionation (CEF) to determine amorphous fraction the selected molecular sizes. See also Roy et al., *Development of Comprehensive Two-Dimensional High Temperature Liquid Chromatography×Gel Permeation Chromatography for Characterization of Polyolefins*, Macromolecules (2010), 43, 3710-3720; Gillespie et al., "APPARATUS AND METHOD FOR POLYMER CHARACTERIZATION", US2008/0166817A1; each incorporated herein by references.

In one embodiment, or a combination of embodiments described herein, the method is selected from the following: i) a crystallization elution fractionation (CEF) chromatography, or ii) a temperature rising elution fractionation (TREF) chromatography.

In one embodiment, or a combination of embodiments described herein, the support material comprises an inert material.

In one embodiment, or a combination of embodiments described herein, the CI value is from 0.70 to 1.20, or from 0.75 to 1.20, or from 0.80 to 1.20, or from 0.85 to 1.20, or from 0.90 to 1.20.

In one embodiment, or a combination of embodiments described herein, the CI value is from 0.70 to 1.15, or from 0.75 to 1.15, or from 0.80 to 1.15, or from 0.85 to 1.15, or from 0.90 to 1.15.

In one embodiment, or a combination of embodiments described herein, the support material comprises spherical particles that have $D_{50}$ value≤100 microns, or ≤80 microns, or ≤60 microns, or ≤40 microns, or ≤20 microns, or ≤10 microns. In a further embodiment, the support material comprises >90 vol % spherical particles. In one embodiment, or a combination of embodiments described herein, the support material comprises spherical particles that have $D_{50}$ value ≥1.0 microns, or ≥2.0 microns, or ≥3.0 microns, or ≥4.0 microns. In a further embodiment, the support material comprises >90 vol % spherical particles.

In one embodiment, or a combination of embodiments described herein, the support material comprises spherical particles that have $D_{50}$ value≤10 microns, or ≤9.0 microns, or ≤8.0 microns, or ≤7.0 microns, or ≤6.0 microns. In a further embodiment, the support material comprises >90 vol % spherical particles. In one embodiment, or a combination of embodiments described herein, the support material comprises spherical particles that have $D_{50}$ value ≥1.0 microns, or ≥2.0 microns, or ≥3.0 microns, or ≥4.0 microns. In a further embodiment, the support material comprises >90 vol % spherical particles.

In one embodiment, or a combination of embodiments described herein, the support material has a $D_{50}$ from 2 to 100 microns, further from 5 to 80 microns, further from 5 to 50 microns. In a further embodiment, the support material comprises >90 vol % spherical particles.

In one embodiment, or a combination of embodiments described herein, the support material has a $D_{50}$ from 2 to 40 microns, further from 5 to 30 microns, further from 10 to 20 microns, further from 2 to 10 microns. In a further embodiment, the support material comprises >90 vol % spherical particles.

In one embodiment, or a combination of embodiments described herein, the support material has a particle size distribution, such that $D_{10} \geq 2$ microns, $D_{90} \leq 3.1 \times D_{50}$, and the ratio of $(D_{90}-D_{10})/D_{50} < 3.0$, further <2.0, further <1.5, and further <1.3. In a further embodiment, the support material comprises >90 vol % spherical particles.

In one embodiment, or a combination of embodiments described herein, the support material comprises one of the following: a) gold particles, b) gold coated particles (for example, gold coated nickel), c) particles comprising gold, d) particles comprising a coating comprising gold, e) copper particles, f) copper coated particles, g) particles comprising copper, h) particles comprising a coating comprising copper, i) silver particles, j) silver coated particles, k) particles comprising silver, l) particles comprising a coating comprising silver or m) a combination thereof. In a further embodiment, the support material comprises ≥90 wt %, or ≥95 wt %, or ≥98 wt %, or ≥99 wt % of the particles, based on the weight of the support material.

In one embodiment, or a combination of embodiments described herein, the support material comprises one of the following: a) gold particles, b) gold coated particles (for example, gold coated nickel), c) particles comprising gold, d) particles comprising a coating comprising gold, e) copper particles, f) copper coated particles, g) particles comprising copper, h) particles comprising a coating comprising copper, or i) a combination thereof. In a further embodiment, the support material comprises ≥90 wt %, or ≥95 wt %, or ≥98 wt %, or ≥99 wt % of the particles, based on the weight of the support material.

In one embodiment, or a combination of embodiments described herein, the support material comprises one of the following: a) gold particles, b) gold coated particles (for example, gold coated nickel), c) particles comprising gold, d) particles comprising a coating comprising gold, or q) a combination thereof. In a further embodiment, the support material comprises ≥90 wt %, or ≥95 wt %, or ≥98 wt %, or ≥99 wt % of the particles, based on the weight of the support material.

In one embodiment, or a combination of embodiments described herein, the support material comprises gold particles, gold coated particles (for example, gold coated nickel), or a combination thereof. In a further embodiment, the support material comprises ≥90 wt %, or ≥95 wt %, or ≥98 wt %, or ≥99 wt % of the particles, based on the weight of the support material.

In one embodiment, or a combination of embodiments described herein, the support material comprises a material comprising at least one inert metal.

In one embodiment, or a combination of embodiments described herein, the "support material" is thermally stable at a temperature range from −15° C. to 230° C. In one embodiment, or a combination of embodiments described herein, the "support material" is chemically stable at a temperature range from −15° C. to 230° C. In one embodiment, or a combination of embodiments described herein, the "support material" is thermally and chemically stable at a temperature range from −15° C. to 230° C.

Chemically stable means that the support material does not undergo chemical reaction with mobile phase or with polymer solution; and does not undergo thermal decomposition. Thermally stable means that the support material does not undergo substantial thermal expansion or contraction, which expansion or contraction causes the column bed to move or to generate voids, or which causes deterioration of the column performance in a relatively short period of time.

In one embodiment, or a combination of embodiments described herein, the support material has a surface coating layer, and wherein the thickness of the coating layer is from 10 nm to 100 nm, or from 20 nm to 100 nm. In one embodiment, or a combination of embodiments described herein, the support material has a surface coating layer, and the thickness of the coating layer is from 5 nm to 200 nm, or from 10 nm to 200 nm, or from 20 nm to 200 nm.

In one embodiment, or a combination of embodiments described herein, for step c), the temperature of the support material is reduced at a rate greater than, or equal to, 0.5° C./min; or greater than, or equal to, 1.0° C./min; or greater than, or equal to, 1.5° C./min; or greater than, or equal to, 2.0° C./min; or greater than, or equal to, 3.0° C./min; or greater than, or equal to, 4.0° C./min; or greater than, or equal to, 5.0° C./min; or greater than, or equal to, 6.0° C./min; or greater than, or equal to, 7.0° C./min; or greater than, or equal to, 8.0° C./min; or greater than, or equal to, 9.0° C./min; or greater than, equal to, 10.0° C./min; or greater than, equal to, 12.0° C./min; or greater than, or equal to, 15.0° C./min; or greater than, or equal to 20.0° C./min; or greater than, or equal to, 25.0° C./min; or greater than, or equal to, 30.0° C./min.

In one embodiment, or a combination of embodiments described herein, for step d), the temperature of the support material is increased at a rate greater than, or equal to, 0.5° C./min; or greater than, or equal to, 1.0° C./min; or greater than, or equal to, 1.5° C./min; or greater than, or equal to, 2.0° C./min; or greater than, or equal to, 3.0° C./min; or greater than, or equal to, 4.0° C./min; or greater than, or equal to, 5.0° C./min; or greater than, or equal to, 6.0° C./min; or greater than, or equal to, 7.0° C./min; or greater than, or equal to, 8.0° C./min; or greater than, or equal to, 9.0° C./min; or greater than, equal to, 10.0° C./min; or greater than, or equal to, 12.0° C./min; or greater than, or equal to, 15.0° C./min; or greater than, equal to 20.0° C./min; or greater than, or equal to, 25.0° C./min; or greater than, or equal to, 30.0° C./min.

A temperature gradient device (for example, a GC oven (Agilent Technologies), used in a CEF from PolymerChar) is an instrument that is used to thermally treat, or cool, a column (for example, a chromatography column) in a controlled manner. Other examples are Hewlett Packard GC ovens, and Analytical TREF ovens (for example, see Gillespie et al., U.S. 2008/0166817A1).

In one embodiment, or a combination of embodiments described herein, for step c), an eluent flow is maintained through the support material. In a further embodiment, the eluent flow through the support material is maintained at a rate less than, or equal to, 0.5 ml/min.

In one embodiment, or a combination of embodiments described herein, for step c) the eluent flow through the support material, is maintained at a rate less than, or equal to, 0.4 mL/min, further less than, or equal to, 0.3 mL/min, further less than, or equal to, 0.2 mL/min, further less than, or equal to, 0.1 mL/min, further less than, or equal to, 0.05 mL/min, further less than, or equal to, 0.02 mL/min, further less than, or equal to, 0.01 mL/min.

In one embodiment, or a combination of embodiments described herein, for step d), an eluent flow rate is maintained through the support material. In a further embodiment, the eluent flow is maintained at a rate from 0.1 to 3.0 mL/min, or from 0.1 to 2.0 mL/min, or from 0.1 to 1.0 mL/min.

In one embodiment, or a combination of embodiments described herein, Soluble Fraction Elution Time is >0 min, or >1.0 minute, or >2.0 minute, or >3.0 minute, or >5.0 minute, or >10 minute, or >15 minute, or >20 minute, or >30 minute.

In one embodiment, or a combination of embodiments described herein, the eluent comprises ≤400 ppm water, or ≤300 ppm water, or ≤200 ppm water, or ≤100 ppm water or ≤50 ppm water, or ≤20 ppm water, or ≤10 ppm water, based on the weight of the solvent.

In one embodiment, or a combination of embodiments described herein, the eluent is selected from the following: 1,2-dichlorobenzene, 1,2,4-trichlorobenzene, tetrachloroethylene, decanol, diphenyl ether, decane, ethylene glycol monobutyl ether (EGMBE), or a mixture thereof.

In one embodiment, or a combination of embodiments described herein, the eluent is selected from the following mixtures: decanol and 1,2,4-trichlorobenzene; decane and 1,2-dichlorobenzene; and ethylene glycol monobutyl ether (EGMBE) and 1,2-dichlorobenzene.

An inventive method may comprise a combination of two or more embodiments as described herein.

Olefin-Based Polymer Composition

In one embodiment, or a combination of embodiments described herein, the olefin-based polymer composition is a "block composite" ("BC") that comprises the following three polymer components:
  (i) an ethylene-based polymer (EP) having an ethylene content from 10 mol % to less than 90 mol % (a soft copolymer), based on the total moles of polymerized monomer units in the ethylene-based polymer (EP);
  (ii) an alpha-olefin-based polymer (AOP) having an alpha-olefin content of greater than 90 mol % (a hard copolymer), based on the total moles of polymerized monomer units in the alpha-olefin-based polymer (AOP); and
  (iii) a block copolymer having an ethylene block (EB) and an alpha-olefin block (AOB); wherein the ethylene block (soft block/soft segment) contains more polymerized ethylene than the alpha-olefin block (hard block/hard segment), and
  wherein the ethylene block has the same or similar Tm as the ethylene-based polymer (EP) of component (i), and
  wherein the alpha-olefin block has the same or similar Tm as the alpha-olefin-based polymer (AOP) of component (ii); and
  wherein the phrase "same or similar" refers to an absolute Tm differential of ≤5° C., further ≤4° C., further ≤3° C., further ≤2° C.

In one embodiment, or a combination of embodiments described herein, the olefin-based polymer composition is a "crystalline block composite" ("CBC") that comprises the following three polymer components:
  (i) a crystalline ethylene based polymer (CEP) having an ethylene content of greater than, or equal to, 90 mol % (also referred to herein as a soft polymer of CBC), based on the total moles of polymerized monomer units in the crystalline ethylene-based polymer (CEP);
  (ii) a crystalline alpha-olefin based polymer (CAOP) having an alpha-olefin content of greater than 90 mol % (also referred to herein as a hard polymer of the CBC), based on the total moles of polymerized monomer units in the crystalline alpha-olefin-based polymer (CAOP); and
  (iii) a block copolymer comprising a crystalline ethylene block (CEB) and a crystalline alpha-olefin block (CAOB); and
  wherein the crystalline ethylene block has the same or similar Tm as the crystalline ethylene-based polymer (CEP) of component (i), and
  wherein the crystalline alpha-olefin block has the same or similar Tm as the crystalline alpha-olefin-based polymer (CAOP) of component (ii); and
  wherein the phrase "same or similar" refers to an absolute Tm differential of ≤5° C., further ≤4° C., further ≤3° C., further ≤2° C.

Suitable alpha-olefins include C3-C10 alpha-olefins, and preferably selected from propylene, 1-butene, 1-hexene, and 1-octene.

In one embodiment, or a combination of embodiments described herein, the olefin-based polymer composition has a density ≥0.855 g/cc, or ≥0.860 g/cc; or ≥0.865 g/cc; or ≥0.870 g/cc (1 cc=1 cm$^3$). In one embodiment, or a combination of embodiments described herein, the olefin-based polymer has a density ≤0.950 g/cc; or ≤0.945 g/cc; or ≤0.940 g/cc, or ≤0.935 g/cc; or ≤0.930 g/cc.

In one embodiment, or a combination of embodiments described herein, the olefin-based polymer has a density ≥0.875 g/cc; or ≥0.880 g/cc; or ≥0.885 g/cc, or ≥0.890 g/cc.

In one embodiment, or a combination of embodiments described herein, the olefin-based polymer composition has a MFR (230° C., 2.16 kg)≤20 g/10 min; or ≤15 g/10 min; or ≤10 g/10 min.

In one embodiment, or a combination of embodiments described herein, the olefin-based polymer composition has a MFR (230° C., 2.16 kg)≥1.0 g/10 min, or ≥2.0 g/10 min, or ≥3.0 g/10 min; or ≥4.0 g/10 min; or ≥5.0 g/10 min.

In one embodiment, or a combination of embodiments described herein, the olefin-based polymer composition has a MFR (230° C., 10.0 kg)≤10 g/10 min; or ≤8.0 g/10 min; or ≤6.0 g/10 min, or ≤4.0 g/10 min.

In one embodiment, or a combination of embodiments described herein, the olefin-based polymer composition has a MFR (230° C., 10.0 kg)≥0.1 g/10 min, or ≥0.2 g/10 min, or ≥0.3 g/10 min, or ≥0.4 g/10 min; or ≥0.5 g/10 min; or ≥0.6 g/10 min.

In one embodiment, or a combination of embodiments described herein, the olefin-based polymer composition has a weight average molecular weight (Mw)≤500,000 g/mole; or ≤450,000 g/mole; or ≤400,00 g/mole.

In one embodiment, or a combination of embodiments described herein, the olefin-based polymer composition has a weight average molecular weight (Mw)≥10,000 g/mole, or ≥20,000 g/mole, or ≥30,000 g/mole, or ≥40,000 g/mole, or ≥50,000 g/mole, or ≥60,000 g/mole, or ≥80,000 g/mole, or ≥100,000 g/mole.

In one embodiment, or a combination of embodiments described herein, the olefin-based polymer composition has a weight molecular distribution (MWD)≤10.00; or ≤9.0; or ≤8.0; or ≤7.0; or ≤6.5; or ≤6.0; or ≤5.5, or ≤5.0; or ≤4.5, or ≤4.0; or ≤3.6, or ≤3.0; or ≤2.9; or ≤2.8.

In one embodiment, or a combination of embodiments described herein, the olefin-based polymer composition has a weight molecular distribution (MWD)≥2.00, or ≥2.10, or ≥2.20, or ≥2.30, or ≥2.40, or ≥2.50, or ≥2.60.

In one embodiment, or a combination of embodiments described herein, the olefin-based polymer composition has two melting temperature, as determined by DSC. In regard to the temperature scale of the DSC profile, a low melting point and a high melting point, In one embodiment, or a combination of embodiments described herein, the olefin-based polymer composition has a highest melting temperature (Tm), in regard to the temperature scale, ≤170° C., or ≤160° C., or ≤150° C.; or ≤145° C.; or ≤140° C.

In one embodiment, or a combination of embodiments described herein, the olefin-based polymer composition has a highest melting temperature (Tm), in regard to the temperature scale, ≥80° C., or ≥90° C., or ≥100° C., or ≥110° C., or ≥120° C.

In one embodiment, or a combination of embodiments described herein, the olefin-based polymer composition has a crystallization temperature (Tc)≤110° C.; or ≤105° C.; or ≤100° C., or ≤95° C.

In one embodiment, or a combination of embodiments described herein, the olefin-based polymer composition has a crystallization temperature (Tc)≥70° C., or ≥75° C., or ≥80° C.

In one embodiment, or a combination of embodiments described herein, the olefin-based polymer composition has a melting enthalpy ≤200 J/g; or ≤150 J/g; or ≤100 J/g, or ≤52 J/g.

In one embodiment, or a combination of embodiments described herein, the olefin-based polymer composition has a melting enthalpy ≥34 J/g, or ≥36 J/g, or ≥50 J/g.

The olefin-based polymer composition may comprise a combination of two or more embodiments as described herein.

Co-Crystallization

In the determination of the comonomer content and distribution analysis (CCD) or short chain branching analysis (SCBD), co-crystallization (also, commonly named as co-elution) refers to the phenomenon that polymer chains (for example, olefin-based polymer chains) with similar, but different, microstructures may form crystals together and/or elute together, leading to errors in the reported CCD or SCBD. Co-crystallization is one of the key factors limiting the resolution and the test accuracy of crystallization-based techniques, which include crystallization analysis fractionation (CRYSTAF, Monrabal, U.S. Pat. No. 5,222,390), temperature rising elution fractionation (TREF, L Wild et al., Advances in Polymer Science 98, Springer-Verlag Berlin Heidelberg GmbH, P21, and reference cited) and crystallization elution fractionation (CEF, Monrabal et al, Macromol. Symp. 257, 71-79 (2007)). Quantifying the degree of co-crystallization in an unknown multi-component system is very challenging. As a result of co-crystallization, it is difficult to model or deconvolute the results from CRYSTAF, TREF, or CEF (a high throughput TREF, which runs a TREF type of experiment at a fraction of conventional TREF analysis time, by having a slow flow during cooling process (Monrabal, EP 2 008 701 B1)).

Co-crystallization is an inherent characteristic of crystallization based separation techniques. It is well known in the art that reducing cooling rate, such as 0.025° C./min, as in the Wild TREF experiment, reduces the amount of co-crystallization. The Wild TREF, using a cooling rate of 0.025° C./min has been widely accepted as the golden standard for SCBD analysis, at a cost of very long analysis time (4500 minutes per samples after sample solution has been loaded to the Wild TREF column).

Definition of Co-Crystallization Index (CI)

The co-crystallization index (CI) is defined as the following, wherein CI=$A_I/A_0$, where $A_I$ is the peak area of the highest temperature elution peak of DOWLEX 2045 or DOWLEX 2056A, obtained from CEF or TREF analysis, and $A_0$ is the peak area of the same peak of the same material, determined by using the experimental conditions of Wild (Wild et al, *Journal of Polymer Science, Poly. Phys. Ed.*, Vol. 20, p. 441 (1982)), using the support material CHROMOSORB® PNAW that has a diameter range from 210 to 250 microns. The support material used for the determination of $A_I$ is not CHROMOSORB PNAW that has a diameter range from 210 to 250 microns.

Either DOWLEX 2045 ((density=0.920 g/cc, I2=1.0 g/10 min, I10/I2=8.0 (target properties)) or DOWLEX 2056A (density=0.920 g/cc, I2=1.0 g/10 min, I10/I2=8.0 (target properties)) can be used to calculate CI. When calculating CI, it is noted that CEF and Wild TREF, or TREF and Wild TREF are performed on the same lot of the same material. The calculation of CI includes the following steps:

(1) Obtain the SCBD distribution by CEF (see Test Methods section below) or TREF (see Test Methods section below), which displays the "$dW_f/dT$ versus elution temperature," where $dW_f/dT$ is the weight fraction ($W_f$) of the polymer eluting at temperature of T;

(2) Determine the elution temperature valley for soluble fraction, $T_{SF}$, where $T_{SF}$ is defined as the elution temperature at which the soluble fraction peak returns to baseline or nearly to baseline. From the SCBD distribution, $T_{SF}$ is the elution temperature at the peak valley between the low integration limit and 40° C. (for example, see FIG. 1);

(3) Determine the elution valley temperature ($T_v$) at the peak valley of the highest temperature elution peak. The valley should lie between 86° C. and 100° C., where it is the minimum height between 86° C. and 100° C. (see FIG. 1);

(4) Calculate the peak area (%) of the highest temperature elution peak ($A_I$):

$$A_I + \frac{\int_{T_v}^{upperintergrationlimit} dW_f/dT * dT}{\int_{T_{SF}}^{upperintergrationlimit} dW_f/dT * dT} * 100\%;$$

Figure 2:
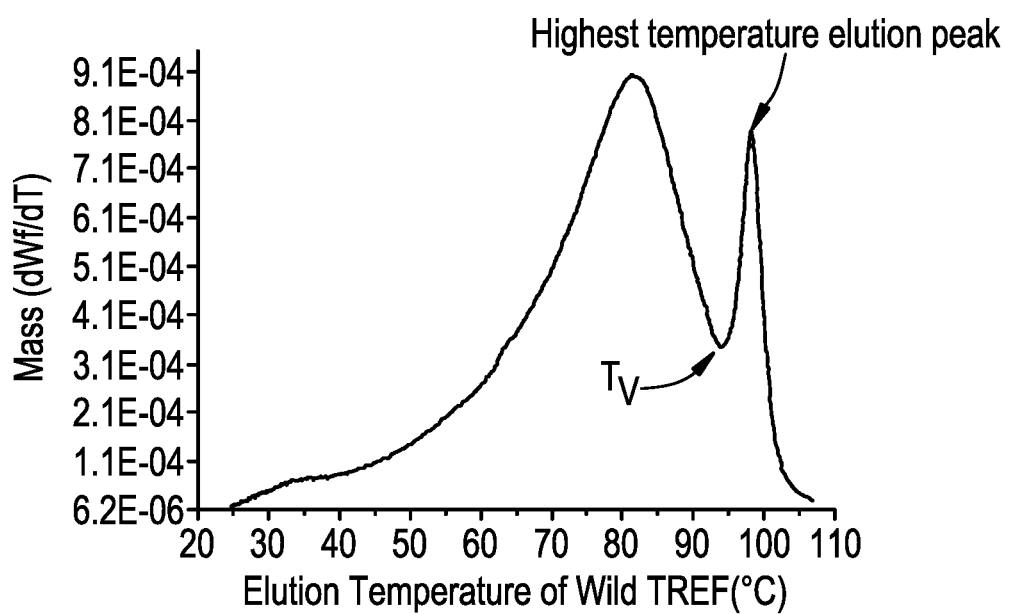
FIG. 2 is a TREF chromatogram of DOWLEX 2056A, which is noted for the calculation of $A_0$. See the discussion of the Co-crystallization Index below.

(5) Obtain the SCBD distribution of the same material by Wild TREF displaying "$dW_f/dT$ versus elution temperature," where $dW_f/dT$ is the weight fraction ($W_f$) of the polymer eluting at elution temperature of T; the elution temperature of isothermal elutions period is extrapolated linearly by using the elution heating rate of 20° C./min;

(6) Determine the elution valley temperature ($T_v$) at the peak valley of the highest temperature elution peak, by searching from the elution temperature from 86° C. toward 100° C., where a peak valley is the minimum height between 86° C. and 100° C. by using SCBD obtained by Wild TREF (for example, see FIG. 2);

(7) Calculate $A_o$ from SCBD distribution obtained with Wild TREF, as follows:

$$A_o = \frac{\int_{T_v}^{107.0} dW_f/dT * dT}{\int_{24.6}^{107.0} dW_f/dT * dT} \times 100\%;$$

(8) Calculate CI from $A_I$ and $A_0$:

$$CI = \frac{A_I}{A_0}.$$

For DOWLEX 2056A, $A_0$ is 13.4%. For example, see FIGS. 1 and 2. For the calculation of $A_I$ from the SCBD distribution obtained from TREF, the sample is DOWLEX 2056A—see FIG. 1. For the calculation of $A_o$ from the SCBD distribution obtained from Wild TREF, the sample is DOWLEX 2056A—see FIG. 2.

DEFINITIONS

Unless stated to the contrary, implicit from the context, or customary in the art, all parts and percents are based on weight, and all test methods are current as of the filing date of this disclosure.

The term "olefin-based polymer composition," as used herein, refers to a composition that comprises ≥98 wt % of one or more olefin-based polymers, and the composition, as a whole, comprises 50 wt %, or a majority amount, of one or more polymerized olefins, based on the weight of the olefin-based polymer composition. In one embodiment, the olefin-based polymer composition comprises 50 wt %, or a majority amount, of polymerized ethylene, based on the weight of the olefin-based polymer composition. In another embodiment, the olefin-based polymer composition comprises 50 wt %, or a majority amount, of polymerized propylene, based on the weight of the olefin-based polymer composition.

As used herein, the term "first elution" refers to the first elution peak due to the first polymer fraction to elute from the support material.

As used herein, the term "lower integration limit," in reference to the first elution peak, refers to the point (lower temperature) of inflection, where the peak profile rises above the baseline of the chromatogram.

As used herein, the term "upper integration limit," in reference to the first elution peak, refers to the point (upper temperature) where the peak profile returns to the baseline of the chromatogram.

The term "wt % "amorphous" fraction," is defined as $\{PA_{amorp}/PA_{total} \times 100\}$ (Eqn. A); wherein $PA_{amorp}$=peak area of the first elution, and $PA_{total}$=total peak area of the polymers of the olefin-based polymer composition.

The term "support material," as used herein, refers to a material which exists, in the fluid stream, as a solid form, in a chromatographic process, including processes that change the temperature of the support material, and/or change the solvent composition.

An inert material, as used herein, in reference to a support material, refers to a material that does not undergo chemical and/or physical transformation when used as a support material or as a component of a support material.

A used herein the term "organic solvent" refers to a liquid (comprises at least one carbon atom), or a mixture of liquids, which can dissolve the olefin based polymer composition, at room temperature or at an elevated temperature, up to the boiling temperature of the solvent. Examples of organic solvents include, but are not limited to, ortho-dichlorobenzene, 1,2,4-trichlorobenzene, tetrachloroethene, 1-bromonaphthalene, diphenol ether, and tetrachloroethene with 1-bromo-naphthalene.

A used herein the term "Soluble Fraction Elution Time" refers to a period of time (in minutes in general) when elution process in TREF and CEF starts, while the temperature of supporting material is kept constant.

The term "eluent," as used herein, refers to a solvent used in a chromatography process to move, or elute, one or more substances from a stationary support material.

The term "spherical particles," as used herein, refers to totally round, or almost round particles with minor surface variations, such that, for a sample of particles containing at least 100 particles, the ratio of largest diameter to the smallest diameter of each particle be less than or equal to two, as determined by scanning electron microscopy.

The term "surface coating layer," as used herein, refers to a coating on the outer surfaces on the particles of a support material. Typically at least 95 area percent of the total surface area of a sample of particles is coated. The amount of surface coating can be determined by SEM (Scanning Electron Microscopy).

The term "polymer," as used herein, refers to a polymeric compound prepared by polymerizing monomers, whether of the same or a different type. The generic term polymer thus embraces the term homopolymer (employed to refer to polymers prepared from only one type of monomer, with the understanding that trace amounts of impurities can be incorporated into the polymer structure), and the term interpolymer as defined hereinafter. Trace amounts of impurities, for example, catalyst residues, may be incorporated into and/or within a polymer.

The term "interpolymer," as used herein, refers to polymers prepared by the polymerization of at least two different types of monomers. The generic term interpolymer includes copolymers (employed to refer to polymers prepared from two different monomers), and polymers prepared from more than two different types of monomers.

The term "olefin-based polymer," as used herein, refers to a polymer that comprises 50 wt %, or a majority amount, of polymerized olefin monomer, for example ethylene or propylene, (based on weight of the polymer) and, optionally, at least one comonomer.

The term "ethylene-based polymer," as used herein, refers to a polymer that comprises 50 wt % or a majority amount of polymerized ethylene monomer (based on weight of the polymer) and, optionally, at least one comonomer.

The term "ethylene-based interpolymer," as used herein, refers to an interpolymer that comprises 50 wt % or a majority amount of polymerized ethylene monomer (based on weight of the interpolymer) and at least one comonomer.

The term "ethylene-based copolymer," as used herein, refers to a copolymer that comprises 50 wt % or a majority amount of polymerized ethylene monomer (based on weight of the copolymer) and one comonomer, as the only two monomer types.

The term "ethylene/α-olefin interpolymer," as used herein, refers to an interpolymer that comprises 50 wt % or a majority amount of polymerized ethylene monomer (based on the weight of the interpolymer) and at least one α-olefin.

The term, "ethylene/α-olefin copolymer," as used herein, refers to a copolymer that comprises 50 wt % or a majority amount of polymerized ethylene monomer (based on the weight of the copolymer), and an α-olefin, as the only two monomer types.

The term, "polyethylene homopolymer," as used herein, refers to a polymer that comprises only polymerized ethylene monomer.

The term "propylene-based polymer," as used herein, refers to a polymer that comprises a majority amount of polymerized propylene monomer (based on weight of the polymer) and, optionally, at least one comonomer.

The term "propylene-based interpolymer," as used herein, refers to an interpolymer that comprises a majority amount of polymerized propylene monomer (based on weight of the inter-polymer) and at least one comonomer.

The term "propylene-based copolymer," as used herein, refers to a copolymer that comprises a majority amount of polymerized propylene monomer (based on weight of the copolymer) and one comonomer, as the only two monomer types.

The term "propylene/α-olefin interpolymer," as used herein, refers to an interpolymer that comprises a majority amount of polymerized propylene monomer (based on the weight of the interpolymer) and at least one α-olefin.

The term, "propylene/α-olefin copolymer," as used herein, refers to a copolymer that comprises a majority amount of polymerized propylene monomer (based on the weight of the copolymer), and an α-olefin, as the only two monomer types.

The term "propylene/ethylene interpolymer," as used herein, refers to an interpolymer that comprises a majority amount of polymerized propylene monomer (based on the weight of the interpolymer) and ethylene.

The term, "propylene/ethylene copolymer," as used herein, refers to a copolymer that comprises a majority amount of polymerized propylene monomer (based on the weight of the copolymer), and ethylene, as the only two monomer types.

The term "composition," as used herein, includes a mixture of materials which comprise the composition, as well as reaction products and decomposition products formed from the materials of the composition.

The term "multidimensional chromatography system," as used herein, refers to the coupling together of multiple separation mechanisms (or chromatographies). See, for example, J. C. Giddings (1990), Use of Multiple Dimensions in Analytical Separations, in Heman Cortes Editor, *Multidimensional Chromatography: Techniques and Applications* (1st ed. pp. 1), New York, NY: Marcel Dekker, Inc.).

The terms "comprising," "including," "having," and their derivatives, are not intended to exclude the presence of any additional component, step or procedure, whether or not the same is specifically disclosed. In order to avoid any doubt, all compositions claimed through use of the term "comprising" may include any additional additive, adjuvant, or compound, whether polymeric or otherwise, unless stated to the contrary. In contrast, the term, "consisting essentially of" excludes from the scope of any succeeding recitation any other component, step or procedure, excepting those that are not essential to operability. The term "consisting of" excludes any component, step or procedure not specifically listed.

The term "temperature gradient chromatography," as used herein, refers to a separation technique, typically a polymer separation, based on a temperature gradient. Preferred examples include TREF and CEF.

The term "TREF," as used herein, refers to Temperature Rising Elution Fractionation chromatography that uses a separation technique based on the different crystallizations of the polymer molecules within a polymer composition, and which uses a static or zero eluent flow during the crystallization (cooling) of the polymer sample onto a stationary support.

The term "CEF," as used herein, refers to Crystallization Elution Fractionation chromatography that uses a separation technique based on the different crystallizations of the polymer molecules within a polymer composition, and which uses a dynamic eluent flow during the crystallization (cooling) of the polymer sample onto a stationary support.

Embodiments of the present disclosure include but are not limited to the following:

1. A method to determine the weight percent of an "amorphous" fraction in an olefin-based polymer composition, comprising one or more olefin-based polymers; said method comprising the following steps:
   a) dissolving the olefin-based polymer composition in organic solvent to form a polymer solution;
   b) injecting at least a portion of the polymer solution onto a support material, and wherein the support material has a Co-crystallization Index (CI) value from 0.70 to 1.20;
   c) cooling the support material at a rate greater than, or equal to, 0.2° C./min;
   d) increasing the temperature of the support material to elute the polymers of the olefin-based polymer composition;
   e) generating a chromatogram;
   f) determining the peak area of the first elution from its lower integration limit to its upper integration limit;
   g) calculating the "amorphous" fraction" based on the following Equation A below:

$$\text{wt \%"amorphous" fraction} = PA_{amorp}/PA_{total} \times 100 \qquad \text{(Eqn. A)};$$

wherein $PA_{amorp}$=peak area of the first elution, and $PA_{total}$=total peak area of the polymers of the olefin-based polymer composition.

2. The method of embodiment 1, wherein the polymer is an olefin-based polymer composition is a "block composite" ("BC") that comprises the following three polymer components:
   (i) an ethylene-based polymer (EP) having an ethylene content from 10 mol % to less than 90 mol % (a soft copolymer), based on the total moles of polymerized monomer units in the ethylene-based polymer (EP);
   (ii) an alpha-olefin-based polymer (AOP) having an alpha-olefin content of greater than 90 mol % (a hard copolymer), based on the total moles of polymerized monomer units in the alpha-olefin-based polymer (AOP); and
   (iii) a block copolymer having an ethylene block (EB) and an alpha-olefin block (AOB); wherein the ethylene block (soft block/soft segment) contains more polymerized ethylene than the alpha-olefin block (hard block/hard segment), and
   wherein the ethylene block has the same or similar Tm as the ethylene-based polymer (EP) of component (i), and
   wherein the alpha-olefin block has the same or similar Tm as the alpha-olefin-based polymer (AOP) of component (ii); and
   wherein the phrase "same or similar" refers to an absolute Tm differential of ≤5° C., further ≤4° C., further ≤3° C., further ≤2° C.

3. The method of embodiment 1, wherein the polymer is an olefin-based polymer composition is a "crystalline block composite" ("CBC") that comprises the following three polymer components:
   (i) a crystalline ethylene based polymer (CEP) having an ethylene content of greater than, or equal to, 90 mol % (also referred to herein as a soft polymer of CBC), based on the total moles of polymerized monomer units in the crystalline ethylene-based polymer (CEP);
   (ii) a crystalline alpha-olefin based polymer (CAOP) having an alpha-olefin content of greater than 90 mol % (also referred to herein as a hard polymer of the CBC), based on the total moles of polymerized monomer units in the crystalline alpha-olefin-based polymer (CAOP); and (iii) a block copolymer comprising a crystalline ethylene block (CEB) and a crystalline alpha-olefin block (CAOB); and wherein the crystalline ethylene block has the same or similar Tm as the crystalline ethylene-based polymer (CEP) of component (i), and wherein the crystalline alpha-olefin block has the same or similar Tm as the crystalline alpha-olefin-based polymer (CAOP) of component (ii); and wherein the phrase "same or similar" refers to an absolute Tm differential of ≤5° C., further ≤4° C., further ≤3° C., further ≤2° C.

4. The method of any one of the previous embodiments, wherein the method is selected from the following: i) a crystallization elution fractionation (CEF) chromatography, or ii) a temperature rising elution fractionation (TREF) chromatography.

5. The method of any one of the previous embodiments, wherein the support material comprises spherical particles that have D50 value less than, or equal to, 100 microns.

6. The method of any one of the previous embodiments, wherein the support material has a CI from 0.70 to 1.20, and wherein the support material comprises an inert material.

7. The method of any one of the previous embodiments, wherein the support material comprises one of the following: a) gold particles, b) gold coated particles, c) particles comprising gold, d) particles comprising a coating comprising gold, e) copper particles, f) copper coated particles, g) particles comprising copper, h) particles comprising a coating comprising copper, or i) a combination thereof.

8. The method of any one of the previous embodiments, wherein the support material comprises one of the following: a) gold particles, b) gold coated particles, c) particles comprising gold, d) particles comprising a coating comprising gold, e) silver particles, f) silver coated particles, g) particles comprising copper, h) particles comprising a coating comprising silver, or i) a combination thereof.

9. The method of any one of the previous embodiments, wherein the first elution has a lower integration limit from 10° C. to 15° C.

10. The method of any one of the previous embodiments, wherein the first elution has an upper integration limit from 30° C. to 45° C., or from 30° C. to 40° C.

11. The method of any one of the previous embodiments, wherein the first elution is integrated from 10° C. to 40° C., or from 12° C. to 40° C., or from 15° C. to 40° C.

12. The method of any one of the previous embodiments, wherein the olefin-based polymer composition comprises two olefin-based polymers.

13. The method of any one of the previous embodiments, wherein the olefin-based polymer composition comprises three olefin-based polymers.

14. The method of any one of the previous embodiments, wherein the support material comprises ≥90 wt %, or ≥95 wt %, or ≥98 wt %, or ≥99 wt % of the particles, based on the weight of the support material.

15. The method of any one of the previous embodiments, wherein the olefin-based polymer composition comprises 50 wt %, or a majority amount, of polymerized ethylene, based on the weight of the olefin-based polymer composition.

16. The method of any one of embodiments 1-14, wherein the olefin-based polymer comprises 50 wt %, or a majority amount, of polymerized propylene, based on the weight of the olefin-based polymer composition.

Test Methods

Crystallization Elution Fractionation (CEF)

The Crystallization Elution Fractionation analysis is conducted according to Monrabal et al, *Macromol. Symp.* 257, 71-79 (2007). The CEF instrument is equipped with a degasser, and equipped with an IR-5 detector (such as that sold commercially from PolymerChar, Spain) and a two angle light scattering detector Model 2040 (such as those sold commercially from Agilent). Ortho-dichlorobenzene (ODCB, 99% anhydrous grade) and Silica gel 40 (particle size 0.2-0.5 mm) (such as commercially available from EMD Chemicals) are obtained. ODCB is further distilled before use. The silica gel is dried in a vacuum oven at 160° C. for at least two hours before use. The ODCB is sparged with dried nitrogen ($N_2$) for one hour before use. Dried nitrogen is obtained by passing nitrogen at <90 psig over dried $CaCO_3$ and 5 Å molecular sieves. The ODCB is further dried by pumping the ODCB through a column or columns packed with dried silica after degasser. Dried ODCB is hereinafter referred to as "ODCB-m." A sample solution is prepared, using the autosampler, by dissolving a polymer sample in distilled ODCB, at 4 mg/ml (32 mg of sample in 8 mL of ODCB-m), under shaking at 160° C. for 60 minutes. The sample solution (300 μL) is injected into the column (see expt. section for column for each analysis). The temperature profile of the CEF is as follows: crystallization at 3.0° C./min, from 95° C. to 30° C.; thermal equilibrium at 30° C. for 0, 1 or 2 minutes; isothermal elution at 30° C. for 2 or 3 minutes, and then at 3.0° C./min from 30° C. to 140° C. The flow rate during crystallization is 0.03 mL/min. The flow rate during elution is 0.50 mL/min. The IR-5 signal data is collected at one data point/second.

Data processing is performed with "GPCOne" software (PolymerChar, Spain). The chromatogram is integrated with "GPCOne" software. A straight baseline is drawn from the visible difference, when the peak falls to a flat baseline at high elution temperature, and the minimum or flat region of detector signal on the low temperature side of the soluble fraction (SF). The upper temperature integration limit is established, based on the visible difference, when the peak falls to the flat baseline region (roughly around 120° C.). The lower temperature integration limit is established, based on the intersection point of baseline with the chromatogram including the soluble fraction. Temperature calibration of the CEF is performed by using a mixture of NIST Standard Reference Material linear polyethylene 1484a (1.0 mg/ml) and EICOSANE (2 mg/ml) in ODCB-m. The calibration consists of four steps: (1) calculating the delay volume defined as the temperature offset between the measured peak elution temperature of EICOSANE minus 30.00° C.; (2) subtracting the temperature offset of the elution temperature from the CEF raw temperature data (it is noted that this temperature offset is a function of experimental conditions, such as elution temperature, elution flow rate, etc.); (3) creating a linear calibration line, transforming the elution temperature across a range from 30.00° C. to 140.00° C., such that NIST linear polyethylene 1484a has a peak temperature at 101.00° C., and EICOSANE has a peak temperature of 30.00° C.; (4) for the soluble fraction measured isothermally at 30° C., linearly extrapolating the elution temperature by using the elution heating rate of 3° C./min. Other linear homopolymer polyethylene samples having an equivalent or similar weight average molecular weight as NIST 1484a (110,000 to 125,000 Daltons) and polydispersity (Mw/Mn from 1.0 to 2.8) can be used.

Temperature Rising Elution Fractionation (TREF)

The TREF experiment and data processing are performed in a manner similar to the CEF, as discussed above, except that the flow rate during cooling is set to zero. The temperature calibration is same as CEF.

Wild TREF

The experimental steps of the temperature rising elution fractionation (TREF) were those as reported according to the Wild publication (Wild et al, *Journal of Polymer Science, Poly. Phys. Ed.*, Vol. 20, p. 441 (1982)).

Temperature Profile of Wild TREF

The temperature profile of Wild TREF is as follows: isothermal cooling at 125° C. for 30 minutes; cooling at 0.125° C./min from 125° C. to 100° C., followed by 0.025° C./min from 100° C. to 25° C.; then thermal equilibrium at 25° C. for 1000 minutes; isothermal elution at 25° C. for 1 minute; and then at 20° C. per hour, from 30° C. to 102° C.; then followed by isothermal elution at 102° C. for 60 minutes. The flow rate during the elution is 4 mL/min.

Detector of Wild TREF

Infrared detector IR4 (PolymerChar, Spain) is used as the detector. The IR4 infrared detector is allowed to stabilize before the analysis. The pump is initiated at 1.0 mL/min, and the flow is increased to 4.0 mL/min over a 5-minute time span. The infrared detector output is zeroed according to the manufacturer's instructions, and the column is purge to equilibrium for at least 30 minutes, until the baseline is essentially flat and changing little, if any. The nominal heating rate is 20° C. per hour during the program.

Particle Size Distribution (D50, D10, D90)

The particle size distribution is measured with an ACCUSIZFR 780 OPTICAL PARTICLE SIZER (Particle Size System, Florida, USA), and uses the principle of Single Particle Optical Sizing (SPOS) to count and size particles, one at a time, thus eliminating missed particles, and providing accurate particle size and count information. The illumination/detection system, in the sensor, is designed to provide a monotonic increase in pulse height with increasing particle diameter. The standard calibration curve is obtained by measuring a series of standard polystyrene latex samples from NIST Traceable Monodisperse Standards (Duke). The detailed procedure for calibration can be found in the operation manual provided by Particle Size System. A particle size distribution (PSD) is constructed by counting a large amount of particles (at least 55,000 particles). The sample (particles) is suspended in methanol (HPLC grade; other suitable solvents include mineral oil or silicon oil), at low enough concentration, to avoid coincidence counting (two particles in sensoring zone), according to the operation procedure provided by Particle Size System. The D50, D10 and D90, each on a volume basis, are calculated by the software of ACCUSIZFR 780. Other solvents suitable include TCB (HPLC grade) and ODCB (HPLC grade). The median diameter (D50, typically in micron), is defined as the particle diameter where half of the mass distribution (volume distribution) resides above this point, and half resides below this point. D10 is defined as the particle diameter where 10% of the mass lies below this point (D10). D90 is defined as the particle diameter that 90 percent of the mass lies below this point (D90).

Electronegativity of the Support Material

The surface property of the support material is first characterized by scanning electron microscopy with energy dispersive X-ray spectroscopy (SEM/EDX). Elemental analysis is performed by using a Bruker AXS X-Flash 30 mm² Silicon Drift Detector (SDD)/EDX system on a FBI Nova NanoSEM 600, equipped with an Everhart-Thornley secondary electron (SE) detector, and a solid state backscatter (BSE) detector operated at a 20 kV accelerating voltage. Instrument conditions are as follows: a working distance of approximately 6-7 mm, aperture No. 5, and spot size 5.5.

Electronegativity of an atom is a measure of the tendency of the atom to attract a bonding pair of electrons. Electronegativity of the support material is determined by each atom identified on the surface of support material by SEM/EDX. The Pauling scale is used. Fluorine (the most electronegative element) is assigned a value of 4.0, and values range down to Cesium and Francium which are the least electronegative, each at 0.7. The values of electronegativity for other atoms are listed in the references (W. W. Porterfield in *Inorganic Chemistry, a Unified Approach*, Addison Wesley Publishing Co., Reading Massachusetts, USA, 1984. A. M. James and M. P. Lord in *Macmillan's Chemical and Physical Data*, Macmillan, London, U K, 1992). Table 1A shows the EXD results (the percentage of the surface components) of the comparative support materials of soda-lime glass with an average particle size (D50) of 125 microns.

TABLE 1A

| | EXD Results | | | | | | | |
| --- | --- | --- | --- | --- | --- | --- | --- | --- |
| Spectrum | C | O | Na | Mg | Al | Si | Cl | Ca |
| Mass % | 1.81 | 31.23 | 9.12 | 1.17 | 0.32 | 42.96 | 0.87 | 6.51 |

Density

Samples are prepared according to ASTM D 1928. Measurements are made within one hour of sample pressing using ASTM D792, Method B.

Melt Index

Melt index, MI or 12, is measured in accordance with ASTM D 1238, Condition 190° C./2.16 kg, and is reported in grams eluted per 10 minutes. The "$I_{10}$" melt index is measured in accordance with ASTM D 1238, Condition 190° C./10 kg, and is reported in grams eluted per 10 minutes. For propylene-based polymers, the melt flow rate (MFR) is measured in accordance with ASTM D-1238, condition 230° C./2.16 kg.

Differential Scanning calorimetry (DSC)

Differential Scanning calorimetry (DSC) is used to measure the heat of fusion, melting temperature and crystallization temperature of polyethylene (PE) based samples and polypropylene (PP) based samples. About five to eight milligrams of sample is weighed and placed in a pan. A lid is crimped against the pan to ensure good thermal contact between the sample and pan. The pan is placed in a DSC cell and then heated from room temperature to 180° C. for ethylene based polymer (230° C. for propylene based) at 50° C./min. The sample is kept at this temperature for five minutes at the end of the first heat scan. The cooling curve is obtained at a rate of 10° C./min from 180° C. to −60° C. for PE (230° C. to −40° C. for PP). The sample temperature is kept isothermal for five minutes at the end of the cooling scan. The second heating curve is obtained at a rate of 10°

C./min to 180° C. for PE (230° C. for PP). The percent crystallinity is calculated by dividing the heat of fusion ($H_f$) measured on the second heat curve, by the heat of fusion of 100% crystalline material, 292 J/g for PE (165 J/g, for PP), and multiplying this quantity by 100 (e.g., for PE, % cryst.=($H_f$/292 J/g)×100; and for PP, % cryst.=($H_f$/165 J/g)× 100).

Unless otherwise stated, melting point(s) ($T_m$) of each polymer is determined from the second heat curve obtained from DSC, as described above. The crystallization temperature ($T_a$) is measured from the first cooling curve.

Gel Permeation Chromatography

The chromatographic system consists of either a Polymer Laboratories Model PL-210 (Agilent) or a Polymer Laboratories Model PL-220 (Agilent) or PolymerChar HT GPC (Spain). The column and carousel compartments are operated at 140° C. Three Polymer Laboratories, 10-μm Mixed-B columns are used with a solvent of 1,2,4-trichlorobenzene. The samples are prepared at a concentration of "0.1 g of polymer" in "50 mL of solvent" or "16 mg of polymer in 8 mL of solvent." The solvent used to prepare the samples contain 200 ppm of BHT. Samples are prepared by agitating lightly for four hours, at 160° C. The injection volume used is "100 microliters," and the flow rate is "1.0 mL/min." Calibration of the GPC column set is performed with twenty one narrow molecular weight distribution polystyrene standards purchased from Polymer Laboratories. The molecular weight (MW) of the standards ranges from 580 to 8,400,000 g/mol, and the standards are contained in six "cocktail" mixtures. Each standard mixture has at least a decade of separation between individual molecular weights. The standards are purchased from Polymer Laboratories (Shropshire, UK). The polystyrene standards are prepared at "0.001 g in 20 mL of solvent" for molecular weights equal to, or greater than, 1,000,000 g/mol, and at "0.005 g in 20 mL of solvent" for molecular weights less than 1,000,000 g/mol.

The polystyrene standard peak molecular weights are converted to polyethylene molecular weights using Equation 1A:

$$M\text{polyethylene} = A(M\text{polystyrene})^B \quad \text{(Eq. 1A)},$$

where M is the molecular weight, A has a value of 0.4316 and B is equal to 1.0 (T. Williams and I. M. Ward, *Polym. Letters*, 6, 621-624 (1968)). A third order polynomial is determined to build the logarithmic molecular weight calibration as a function of elution volume. Polyethylene equivalent molecular weight calculations are performed using VISCOTEK TriSEC software Version 3.0 for Agilent GPC instrument or GPCOne software for PolymerChar GPC instrument.

Gel Permeation Chromatography (3D-GPC)

The chromatographic system consisted of a PolymerChar GPC-IR (Valencia, Spain) high temperature GPC chromatograph equipped with an internal IR5 infra-red detector (IR5) coupled to a Precision Detectors (Now Agilent Technologies) 2-angle laser light scattering (LS) detector Model 2040. For all Light scattering measurements, the 15 degree angle is used for measurement purposes. The autosampler oven compartment was set at 160° Celsius and the column compartment was set at 150° Celsius. The columns used were 4 Agilent "Mixed A" 30 cm 20-micron linear mixed-bed columns. The chromatographic solvent used was 1,2,4 trichlorobenzene and contained 200 ppm of butylated hydroxytoluene (BHT). The solvent source was nitrogen sparged. The injection volume used was 200 microliters and the flow rate was 1.0 milliliters/minute.

Calibration of the GPC column set was performed with at least 20 narrow molecular weight distribution polystyrene standards with molecular weights ranging from 580 to 8,400,000 and were arranged in 6 "cocktail" mixtures with at least a decade of separation between individual molecular weights. The standards were purchased from Agilent Technologies. The polystyrene standards were prepared at 0.025 grams in 50 milliliters of solvent for molecular weights equal to or greater than 1,000,000, and 0.05 grams in 50 milliliters of solvent for molecular weights less than 1,000, 000. The polystyrene standards were dissolved at 80° C. with gentle agitation for 30 minutes. The polystyrene standard peak molecular weights were converted to polyethylene molecular weights using EQ1 (as described in Williams and Ward, J. Polym. Sci., Polym. Let., 6, 621 (1968)): $M_{polyethylene} = A \times (M_{polystyrene})^B$ (EQN 1), where M is the molecular weight, A has a value of 0.4315 and B is equal to 1.0.

A fifth order polynomial was used to fit the respective polyethylene-equivalent calibration points. A small adjustment to A (from approximately 0.415 to 0.44) was made to correct for column resolution and band-broadening effects such that NIST standard NBS 1475 is obtained at 52,000 Mw.

Samples were prepared in a semi-automatic manner with the PolymerChar "Instrument Control" Software, wherein the samples were weight-targeted at 2 mg/ml, and the solvent (contained 200 ppm BHT) was added to a pre nitrogen-sparged septa-capped vial, via the PolymerChar high temperature autosampler. The samples were dissolved for 2 hours at 160° Celsius under "low speed" shaking.

The calculations of $Mn_{(GPC)}$, $Mw_{(GPC)}$, and $Mz_{(GPC)}$ were based on GPC results using the internal IR5 detector (measurement channel) of the PolymerChar GPC-IR chromatograph according to Equations 2-4, using PolymerChar GPCOne™ software, the baseline-subtracted IR chromatogram at each equally-spaced data collection point (i), and the polyethylene equivalent molecular weight obtained from the narrow standard calibration curve for the point (i) from EQN 1:

$$Mn_{(GPC)} = \frac{\sum_i IR_i}{\sum_i (IR_i / M_{polyethylene_i})}, \quad \text{(EQN 2)}$$

$$Mw_{(GPC)} = \frac{\sum_i (IR_i * M_{polyethylene_i})}{\sum_i IR_i}, \quad \text{(EQN 3)}$$

$$Mz_{(GPC)} = \frac{\sum_i (IR_i * M_{polyethylene_i}^2)}{\sum_i (IR_i * M_{polyethylene_i})}. \quad \text{(EQN 4)}$$

In order to monitor the deviations over time, a flow rate marker (decane) was introduced into each sample via a micropump controlled with the PolymerChar GPC-IR system. This flow rate marker (FM) was used to linearly correct the pump flow rate (Flowrate(nominal)) for each sample by retention volume (RV) alignment of the respective decane peak within the sample (RV(FM Sample)) to that of the decane peak within the narrow standards calibration (RV (FM Calibrated)). Processing of the flow marker peak was done via the PolymerChar GPCOne™ Software. Acceptable flow rate correction is such that the effective flow rate should be within +/−2% of the nominal flow rate. The Systematic Approach for the determination of multi-detector offsets is done in a manner consistent with that published by Balke, Mourey, et. al. (Mourey and Balke, Chromatography Polym. Chpt 12, (1992)) (Balke, Thitiratsakul, Lew, Cheung, Mourey, Chromatography Polym. Chpt 13, (1992)), optimizing triple detector log (MW and IV) results from a broad homopolymer polyethylene standard (Mw/Mn>3) to the narrow standard column calibration results from the narrow standards calibration curve using PolymerChar GPCOne™ Software.

The absolute molecular weight data was obtained in a manner consistent with that published by Zimm (Zimm, B. H., J. Chem. Phys., 16, 1099 (1948)) and Kratochvil (Kratochvil, P., Classical Light Scattering from Polymer Solutions, Elsevier, Oxford, NY (1987)) using PolymerChar GPCOne™ software. The overall injected concentration, used in the determination of the molecular weight, was obtained from the mass detector area and the mass detector constant, derived from a suitable linear polyethylene homopolymer, or one of the polyethylene standards of known weight-average molecular weight. The calculated molecular weights (using GPCOne™) were obtained using a light scattering constant, derived from one or more of the polyethylene standards mentioned below, and a refractive index concentration coefficient, dn/dc, of 0.104. Generally, the mass detector response (IR5) and the light scattering constant (determined using GPCOne™) should be determined from a linear standard with a molecular weight in excess of about 50,000 g/mole. The viscometer calibration (determined using GPCOne™) can be accomplished using the methods described by the manufacturer, or, alternatively, by using the published values of suitable linear standards, such as Standard Reference Materials (SRM) 1475a (available from National Institute of Standards and Technology (NIST)). A viscometer constant (obtained using GPCOne™) is calculated which relates specific viscosity area (DV) and injected mass for the calibration standard to its intrinsic viscosity. The chromatographic concentrations are assumed low enough to eliminate addressing 2nd viral coefficient effects (concentration effects on molecular weight). Other respective moments, $Mn_{(Abs)}$ and $Mz_{(Abs)}$ are be calculated according to EQN 5 and EQN 6 as follows:

$$Mn_{(Abs)} = \frac{\sum_i 1 \cdot IR_i}{\sum_i (IR_i / M_{Absolute_i})}, \quad (EQN\ 5)$$

$$Mz_{(Abs)} = \frac{\sum_i 1 \cdot (IR_i * M^2_{Absolute_i})}{\sum_i (IR_i * M_{Absolute_i})}. \quad (EQN\ 6)$$

Experimental

Materials

DOWLEX 2045 Polyethylene Resin or DOWLEX 2056A Polyethylene Resin are the commercial products available from The Dow Chemical Company.

Four block composites (BC1, BC2, BC3, BC4) were made by The Dow Chemical Company (see, for example, U.S. Pat. No. 8,802,774). Each of B1-BC4 was, independently, an olefin-based polymer composition (comprising ≥98 wt % of one or more olefin-based polymers), and the composition, as a whole, comprises a 50 wt % or a majority amount of a polymerized olefin.

Representative Polymerization

BC2 was prepared with the reaction conditions of Table 1B with two reactors in series (loop followed by a CSTR). The catalyst was ([[rel-2',2'"-[(1R,2R)-1,2-cylcohexanediyl-bis(methyleneoxy-κO)] bis[3-(9H-carbazol-9-yl)-5-methyl [1,1'-biphenyl]-2-olato-κO]](2-)]dimethyl-hafnium).

Cocatalyst-1 was a mixture of methyldi(C14-18 alkyl)ammonium salts of tetrakis(pentafluorophenyl)-borate, prepared by reaction of a long chain trialkylamine (Armeen™ M2HT, available from Akzo Nobel, Inc.), HCl and Li[B (C6F5)4], substantially as disclosed in U.S. Pat. No. 5,919, 983, Ex. 2, which were purchased from Boulder Scientific and used without further purification. Cocatalyst-2 was modified methylalumoxane (MMAO), which was purchased from Akzo Nobel and used without further purification. "DEZ" refers to chain shuttling agent diethylzinc. The measured properties of BC 1, BC 2, BC3 and BC 4 are provided in Table 2.

TABLE 1B

| Material | BC 2 | |
|---|---|---|
| Reactor | $1^{st}$ Reactor | $2^{nd}$ Reactor |
| Reactor Control Temp (° C.) | 104.99 | 116.70 |
| Solvent Feed (lb/hr) | 228.57 | 170.52 |
| Propylene Feed (lb/hr) | 7.49 | 23.17 |
| Ethylene Feed (lb/hr) | 14.01 | 0.50 |
| Hydrogen Feed (SCCM) | 0.00 | 0.00 |
| Reactor Ethylene Conc. (g/L) | 1.52 | 0.00 |
| Reactor Propylene Conc. (g/L) | 2.46 | 6.38 |
| Catalyst Efficiency (gPoly/gM) *1.0E6 | 2.55 | 0.70 |
| Catalyst Flow (lb/hr) | 0.20 | 0.75 |
| Catalyst Conc. (ppm) | 39.92 | 39.92 |
| Cocatalyst-1 Flow (lb/hr) | 0.22 | 0.40 |
| Cocatalyst-1 Conc. (ppm) | 499.98 | 999.97 |
| Cocat.-2 Flow (lb/hr) | 0.30 | 0.19 |
| Cocat.-2 Conc. (ppm) | 498.03 | 244.13 |
| DEZ Flow (lb/hr) | 0.22 | 0.00 |
| DEZ Conc. (ppm) | 20000.00 | 0.00 |

TABLE 2

| Sample | MFR (230° C./ 2.16 kg), g/10 min | MFR (230° C./ 10 kg), g/10 min | Mw (kg/mol) (LS Mw) | Mw/Mn | Total wt % C2 (NMR) | Tm (° C.) peak 1/ peak 2 | Tc (° C.) | Melt Enthalpy, J/g |
|---|---|---|---|---|---|---|---|---|
| BC1 | 6.5 | N/M | 124 | 2.34 | 31.7 | 43/136 | 91 | 44 |
| BC2 | N/M | 3.6 | 356 | 2.71 | 34.6 | 26/127 | 92 | 40 |
| BC3 | 7.0 | 0.74 | 143 | 2.40 | 31.5 | 31/127 | 84 | 44 |
| BC4 | 8.3 | 0.74 | 126 | | | | | |

N/M = Not Measured

Column Preparation and Determination of CI
Hardware for Packing Columns—CEF and TREF for CI Measurement and APM of the Inventive Method and Comparative Method Stainless steel column, frit, end fitting of the column were obtained from Agilent Technologies (previously PolymerLab Inc.). An Agilent Model 1100 Liquid Chromatography Pump was used for the slurry packing method. TCB (1,2,4-trichlorobenzene) was the slurry medium. A slurry packing reservoir was constructed of "0.46 cm" internal diameter stainless steel tubing with Valco end fittings. The reservoir was 100 mm in length. A standard ¼" outside diameter tube union was used to connect the packing reservoir to the empty analytical column.

Methodologies for Packing Columns (Inventive and Comparative) CEF and TREF

The columns for use in CEF and TREF included the following:
1. Packed columns that exhibit good mass transfer properties, including low back pressure at standard operating conditions of flow and temperature, low sensitivity to shock from abruptly changing conditions, and lack of channels and void spaces.

Packed columns have sufficient internal liquid volume to permit the studies of the effect of dynamic cooling on component resolution. The dynamic cooling was a process of using a slow flow during the cooling process of CEF (Monrabal et al, *Macromol. Symp.* 257, 71-79 (2007)). Two methodologies of preparing columns were used: (1) dry packing by using the tap-and-fill method, in which the added material was settled by tapping the column, or using an electric vibrating tool; and (2) slurry packing method, which uses a suspension or slurry of the substrate, where the slurry was pumped into the column under flowing conditions (Striegel, Yau, et al., *Modern Size Exclusion Liquid Chromatography*, Wiley, the $2^{nd}$ edition, Chapter 6).

For the dry packing approach, simple tap-and-fill method, the column was suspended vertically. Packing material was added in small increments through a funnel, while the column being tapped or vibrated to settle the substrate. When the packing material was level with the end of the column, the end fitting was added, and the column was tightened. It was a standard practice to condition the columns prior to use, and to inspect the bed for settling or voids. If voids were found, more packing material was added to level the end of the column.

For the slurry packing method, the substrate materials (also commonly called packing materials) were dry added to the empty column and reservoir. The reservoir and column with end fitting was then assembled, and connected to the Agilent pump. TCB (1,2,4-trichlorobenzene) was pumped upward, at a flow of 1 mL/min, through the reservoir, until air was displaced from the column. The flow was momentarily stopped, the column and reservoir was then inverted to a down-flow position. TCB was pumped at 2-5 mL/min through the column for at least twenty minutes, or until the system pressure reaches 2500 PSIG. The column was disconnected from the packing reservoir, and any excess packing material at the end of the column was removed with a flat blade scraper, to provide an even level with the end of the tubing. The end fitting was tightened into place, and the column was ready for conditioning.

Column Conditioning (Comparative and Inventive) CEF and TREF for CI Measurement and APM of the Inventive Method and Comparative Method The newly packed column was installed in the CEF or TREF chromatograph, and flow was established at 0.1 mL/min at room temperature. Depending on the material, and how efficiently it was packed, the back pressure at this point was usually 2-20 Bars. The flow was increased in steps of 0.1 mL/min, allowing the pressure to stabilize between each increase, up to either 0.7 or 1.0 mL/min. The column temperature was increased to 60° C., and then a linear temperature ramp was used to heat the column, under flow, to 140° C. at 10° C./min. This final temperature was held for 20 minutes, and then the column was cooled at 10° C./min to 100° C., and ready for testing.

Column Loading and Crystallization Steps for Wild TREF (Same for Both Comparative and Inventive, Except for Support Material)

The column used for the experiment was a "5 inches by 1 inch (L/W)," made of stainless steel, and capped with Valco 1" diameter frits, radial distributors, and end fettlings. The end fittings were connected to 1/16" Valco stainless steel ferrules and nuts. The packing material was CHROMOSORB™ PNAW solid phase support, received in the 60 to 80 mesh size range, and screened through a 70 mesh sieve to remove fines, so the support was nominally 70 to 80 mesh. One 5" length of 1" OD stainless steel (SS) tubing was cleaned, followed by a final acetone rinse, and air dry. On each end of the tube, the end fitting retainer nut and ferrule were installed. On one end, the end fitting, containing in order, the radial distribution plate, followed by the fritted filter disk were placed; and the end fitting was tightened using a vice and wrench. The column packing, CHROMOSORB PNAW 60/80 MESH (non-acid washed) (fractionated as above), was weighed (24 grams) into a disposable pan.

The column set was clamped vertically, with the end fitting on the bottom. A second 5" lengths of 1" tubing was added at the top of the column using one inch union. Packing material (24 grams) (CHROMOSORB PNAW 60/80 MESH (non-acid washed) (fractionated as above) was also added. A vacuum line (approximately −20 inches of Hg) was connected to the original lower end fitting, but a vacuum was not applied as yet. Acetone (20 mL) was added to the open 1" tube, place the end fitting with a plug on the open tube. The joined tubes were inverted, with mild shaking several times, to disperse the packing and acetone, and the tubes were placed back in the original vertical position. The upper end fitting was removed, and the vacuum source was opened, pulling acetone into a suitable receiver using above vacuum. Small volumes (1-2 ml) of acetone were added to the open, top tube, to rinse the walls and help to settle the packing. When the liquid sank below the level of the packing, and all the packing was settled into the bed, the vacuum source was turned off and disconnected, before replacing the plug in the lower end fitting. The retainer nuts were carefully unscrewed, holding the column union in place, and the two columns were separated. With a flat blade spatula, any excess packing was scraped away, leaving a leveled surface of packing at the tube end. The remaining clean, assembled end fitting was placed on the column, and both end fittings were tightened with a wrench. The packed column was connected to the HPLC pump, with an exit line from the column to a waste receiver. TCB, at approximately 0.5 mL/min, was pumped through the column, gradually increasing the flow rate to 4.0 mL/min, over a 20 minute period, while observing the column for leaks, and retighten the end fittings if necessary. The column was now ready for use.

Sample (Polymer Solution) Loading for Wild TREF (Comparative and Inventive)

Prior to loading the sample onto the column, a polymer solution was prepared at 0.5% by weight, in 1,2,4-trichlorobenzene (TCB), at 160° C. for two hours. The column was heated to 130° C. in an oil bath. Using a vacuum line, about 20 mL of hot TCB was pulled through the column to heat the sample transfer line. Then the vacuum was used to pull 20 mL of sample solution through the column, followed by 2 mL of hot TCB to clear the line.

Properties of Support Materials of CEF and TREF of CI Measurement

Glass beads at 125 microns, were purchased from MO-SCI Specialty Products (4040 HyPoint North, Rolla, MO 65401 USA), with the part number of GL0191B6/125AW. The particle size was 125 µm±6%, with a spherical percentage ≥90% according to MO-SCI Specialty Products.

Soda lime, solid glass microsphere particles (Catalogue #P 2015SL), with a particle size D50 of 8 to 12 microns, were purchased from Cospheric LLC (Santa Barbara, CA, USA).

Solid glass particles with a particle size 23-27 microns, respectively, were purchased from Cospheric LLC (Santa Barbara, CA, USA). The particles in the specified size range were reported as >90%, which means that greater than 90% of the particles fell with the respective diameter size for each grade.

Gold coated nickel particles had D50 of 10.5 microns, D10 of 8.5 microns, and D90 of 13.4 microns. Gold coated nickel particles were purchased from Oerlikon Metco (Canada) Inc., and from Nippon Chemical Industrial Company. The specific surface area reported by the manufacturer was 0.08 m$^2$/g for the gold coated nickel from Nippon Chemical Industrial Company.

Table 3 shows the characteristics of the support materials used in the inventive method and comparative method. Copper particles (averaged particle size D50 10 microns) were purchased from Alfa Aesar.

TABLE 3

Support Materials

| Support Material (SM) | Averaged particle diameter (microns) | Electro-negativity | Surface stability | Porous | Packing method |
|---|---|---|---|---|---|
| A soda-lime glass microsphere | 8-12 D50 | 0.93(Na), 1.31(Mg), 1.00(Ca), 1.50(Al) | Unstable in acidic condition | None | Slurry packing |
| D Solid glass particles | 27 (D50) | 0.93(Na), 1.31(Mg), 1.00(Ca), 1.50(Al) | Unstable in acidic condition | None | Slurry packing |

Chromatography Analyses—Amorphous Peak Measurement (APM) of the Inventive Method Table 4 shows CI for different support materials used to pack columns to perform APM analysis. The measurement was performed with Crystallization Elution Fractionation (CEF) (see above). A guard column packed with 20-27 micron glass (MoSCi Corporation, USA) in a 10 cm (length)×¼" (ID) stainless was installed just before IR-5 detector in the detector oven. The temperature profile was: crystallization at 3° C./min from 105° C. to 30° C., the thermal equilibrium at 30° C. for 2 minute (including "Soluble Fraction Elution Time" being set as two minutes), elution at 3° C./min from 30° C. to 140° C. The flow rate during crystallization is 0.00 ml/min. The flow rate during elution is 0.50 ml/min. The data was collected at one data point/second.

The column was packed with gold coated nickel particles (Bright 7GNM8-NiS, Nippon Chemical Industrial Co.) in a 15 cm (length)×¼" (ID) stainless tubing. The column packing and conditioning were with a slurry method. The final pressure with TCB slurry packing was 150 Bars.

Column temperature calibration was performed by using a mixture of the Reference Material Linear homopolymer polyethylene (having zero comonomer content, Melt index ($I_2$) of 1.0, polydispersity $M_w/M_n$ approximately 2.6, by gel permeation chromatography (1.0 mg/ml), and EICOSANE (1 mg/ml) in ODCB. A temperature calibration consisted of four steps: (1) Calculating the delay volume defined as the temperature offset between the measured peak elution temperature of EICOSANE minus 30.0° C.; (2) Subtracting the temperature offset of the elution temperature from APM raw temperature data. It is noted that this temperature offset is a function of experimental conditions, such as elution temperature, elution flow rate, etc.; (3) Creating a linear calibration line transforming the elution temperature across a range of 30.0° C. and 140.0° C. so that the linear homopolymer polyethylene reference had a peak temperature at 101.0° C., and EICOSANE had a peak temperature of 30.0° C.; (4) For the soluble fraction measured isothermally at 30° C., the elution temperature below 30.0° C. is extrapolated linearly by using the elution heating rate of 3° C./min according to the reference (Cerk and Cong et al., U.S. Pat. No. 9,688,795).

Figure 3:
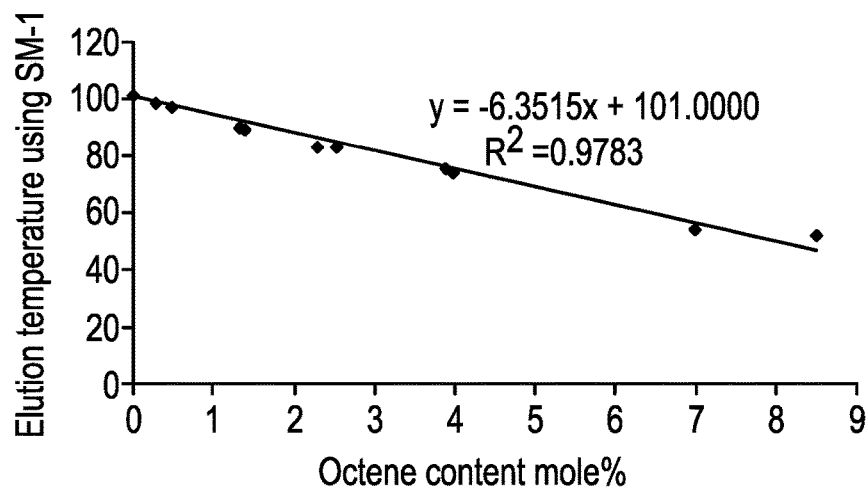
FIG. 3 is the correlation of elution temperature versus octene content in ethylene-octene copolymer using SM-1 supporting material.

The comonomer content versus elution temperature of APM using SM-1 was constructed by using 12 reference materials (ethylene homopolymer and ethylene-octene random copolymer made with single site (CGC) catalyst, having ethylene equivalent weight average molecular weight ranging from 35,000 to 128,000). All of these reference materials were analyzed same way as specified previously at 4 mg/mL. The reported elution peak temperatures followed the correlation in FIG. 3 of octene mole % versus elution temperature of APM at $R^2$ of 0.978.

TABLE 4

CI Results of Various Support Materials measured by CEF

| | Support material (SM) | Averaged particle size D50 (microns) | Co-crystallization index (CI) | Cooling rate of the substrate material, ° C./min | Heating rate of the substrate material, ° C./min | Column dimension ID × Length (cm × cm) | Flow rate during cooling process, ml/min |
|---|---|---|---|---|---|---|---|
| 1 | Gold coated nickel particles (Bright 7GNM8-NiS) | 10 | 0.92 | 3.0 | 3.0 | 0.46 × 25 | 0.03 |

TABLE 4-continued

CI Results of Various Support Materials measured by CEF

|   | Support material (SM) | Averaged particle size D50 (microns) | Co-crystallization index (CI) | Cooling rate of the substrate material, °C./min | Heating rate of the substrate material, °C./min | Column dimension ID × Length (cm × cm) | Flow rate during cooling process, ml/min |
|---|---|---|---|---|---|---|---|
| 2 | Spherical gold particles | 6.2 | 0.94 | 3.0 | 3.0 | 0.46 × 25 | 0.03 |
| 3 | Copper particle | 10 | 1.12 | 3.0 | 3.0 | 0.46 × 25 | 0.03 |
| A | Soda-lime glass microsphere | 8-12 | 1.70 | 3.0 | 3.0 | 0.46 × 25 | 0.03 |
| B | Coated soda-lime glass microsphere | 8.5-12 | 1.70 | 3.0 | 3.0 | 0.46 × 25 | 0.03 |
| C | Soda-lime glass microsphere | 125 | 1.80 | 3.0 | 3.0 | 0.46 × 25 | 0.05 |
| D | Solid glass particle | 27 | 1.41 | 3.0 | 3.0 | 0.46 × 25 | 0.03 |

The calculation of amorphous fraction includes the following steps.

(1) Obtain the chromatogram by APM, which displays the "$dW_f/dT$ versus elution temperature," where $dW_f/dT$ is the weight fraction ($W_f$) of the polymer eluting at temperature of T.

(2) Draw a straight baseline for the whole chromatogram (including first elution peak and the rest of elution peak or peaks), where the beginning point of the line falls into a flat region of the concentration detector signal before all of the elution peaks (including the first elution peak); the ending point of the line falls into a flat region of the concentration detector signal after all of the elution peaks.

(3) Integrate the "baseline subtracted chromatogram" for the entire elution temperature range. The upper temperature integration limit is established, based on the visible difference, when the peak falls to the flat baseline region (roughly around 120° C. for ethylene based polymers, and roughly up to 150° C. for propylene based polymers). The lower integration limit is established, based on the intersection point of the baseline with the chromatogram including the first elution peak.

Figure 4:
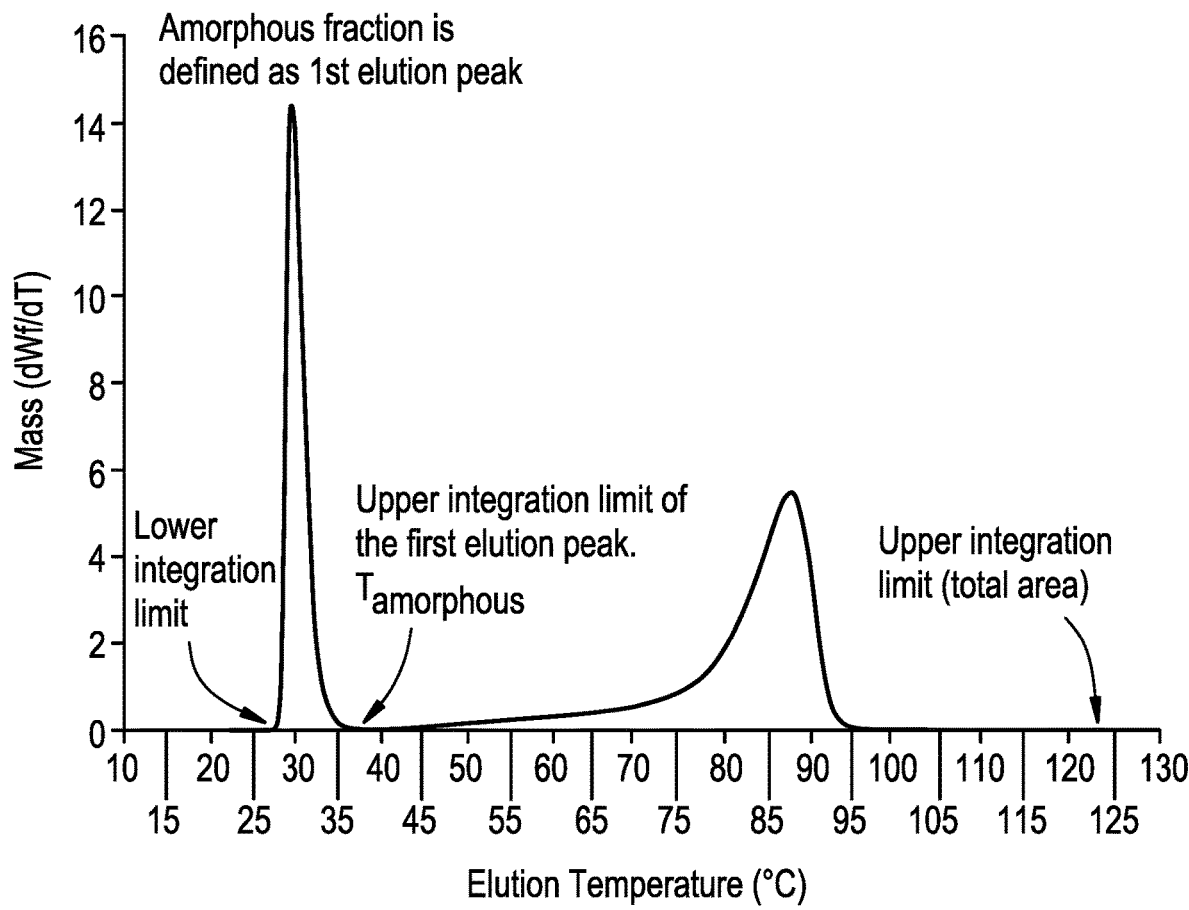
FIG. 4 is the chromatogram of BC-2 obtained by using SM-1 supporting material.

(4) Determine the upper elution limit for the first elution peak. It represents the intersection where a straight baseline falls into a flat region or the minimum of the concentration detector signal right after the first elution peak but before the rest of elution peak or the rest of the elution peaks. When chromatogram is processed, with respect of elution temperature, instead of elution time or elution volume, the upper elution limit for the first elution peak is the elution temperature valley for amorphous component, $T_{amorphous}$, where $T_{amorphous}$ is defined as the elution temperature at which the peak of amorphous component (the first elution peak) returns to the baseline or nearly to baseline at the minimum before the rest of elution peak or peaks. From APM chromatogram, $T_{amorphous}$ is the elution temperature at the peak valley between the low integration limit and 40° C. (for example, see FIG. 4).

(5) Calculate the peak area (%) of amorphous peak ("GPCOne" software (PolymerChar, Spain)).

(6) Calculate weight fraction of amorphous peak as follows ("GPCOne" software (PolymerChar, Spain));

(Equation 1)

$$\text{Wt \% "amorphous fraction"} = \frac{\text{Peak area of amorphrous fraction }(PA_{morphous})}{\text{Peak area of the total elution profile }(PA_{total})} \times 100 =$$

$$\frac{\int_{lowerintergrationlimit}^{T_{amorphous}} dW_f/dT * dT}{\int_{lowerintergrationlimit}^{upperintergrationlimit} dW_f/dT * dT} \times 100.$$

Amorphous Peak Measurement (APM) of the Comparative Method

The APM of the comparative method uses the exact same experimental parameters and condition except for the packing materials.

Xylene Soluble (XS) Fractionation Analysis (ASTM D5492-17)

A weighed amount of resin (Table 1B "sample size", according to ASTM D5492-17) was dissolved in 200 ml o-xylene under reflux conditions. The solution was then cooled in a temperature controlled water bath to 25° C. for 60 minutes to allow the crystallization of the xylene insoluble (XI) fraction. Once the solution was cooled and the insoluble fraction precipitates from the solution, the separation of the xylene soluble (XS) fraction from the xylene insoluble fraction (XI) was done by filtration through a filter paper. The remaining o-xylene in xylene solution was evaporated from the filtrate, dried according ASTM D5492-17.

Comparison of Above Test Methods to Determine "Wt % Amorphous Fraction"

Figure 5:
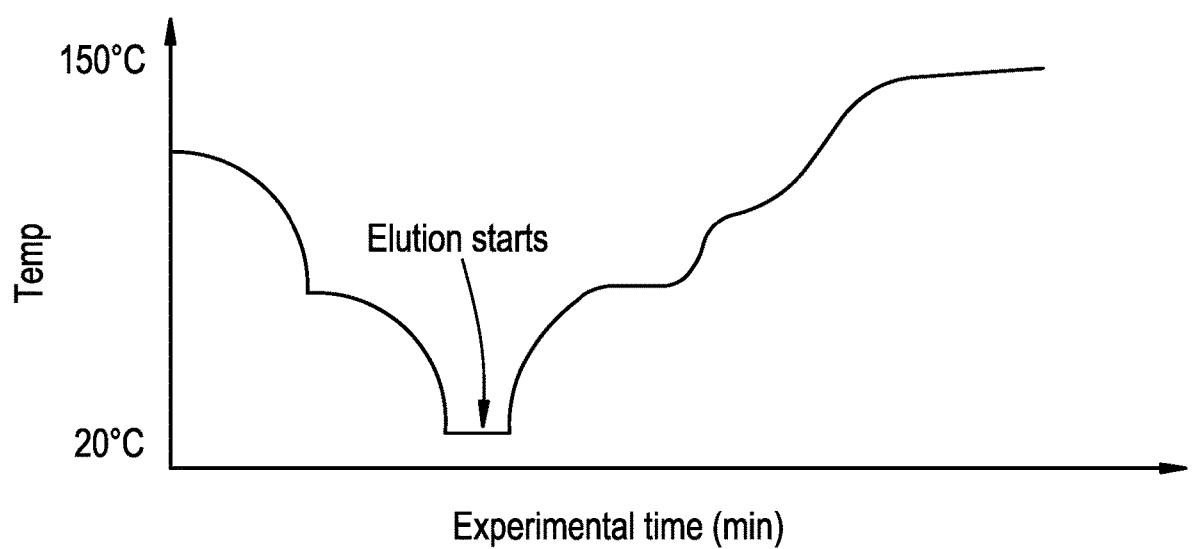
FIG. 5 is the example of temperature profile using in measuring amorphous fraction.

Gold coated nickel particle (SM-1, Bright 7GNM8-NiS) and comparative material of glass bead (SM-A, PL 2015, average particle diameter D50 of 8.5-12 microns) were used to measure amorphous fraction % of each of the block composite materials (BC1, BC2, BC3 and BC4). The xylene soluble fraction measured according to ASTM D5492-17 is shown in Table 5. The inventive method, using the gold coated nickel particle (Bright 7GNM8-NiS) led to an amorphous fraction wt % equal to, or very close to, that obtained using ASTM D5492-17, where the compara-tive material gave the amorphous fraction % which was not correlated with XS % by ASTM D5492-17. Due to the unique surface property of the inventive material, which promotes the crystallization process of polymer chains, thus leading to an accurate measurement of amorphous fraction remaining in the solution at 30° C. This eliminates the needs of using sub ambient temperature, and or use extended time at low temperature to promote the crystallization of polyolefin chains especially with a relatively high comonomer content. In addition, the invention method used commercial instrument to perform the test. Sample dissolution was prepared by autosampler. The testing (excluding the dissolution time) was 63 minutes, while ASTM D5492-17 take at least six hours per sample with each step performed by operator. Supporting materials with a low CI promotes the crystallization, thus allow a further increase in heating and cooling rates for APM analysis. As shown in FIG. 5, a further reduction of analysis can be achieved by optimizing cooling and heating rates, the time of period for isothermal elution (Soluble fraction Elution Time), the column size and flow rates. With IR-5 detector online, the chemical composition (ethylene content %) can be readily obtained by using two channel signals (Lee, et al, Analytical chemistry, 2014, 86, 8649). In the case olefin-based polymers are blended with significant amount of filler (for example, more than 2 wt % fillers, weight of filler divided by total weight of filler and polymers), removing filler by filtering the sample solution before APM measurement is an option.

TABLE 5

CI Results of various Support Materials measured by CEF

| XS % by ASTM 5492-17 * | Amorphous fraction measured using SM-1 (CI of 0.92) * | Amorphous fraction measured using SM-3 (CI of 1.12) * | Amorphous fraction measured using SM-A (CI of 1.70) * | Amorphous fraction measured using SM-D (CI of 1.41) ** |
|---|---|---|---|---|
| BC1 | (33.46 ± 0.81)% | (36.54 ± 0.14)% | 34.96% | (42.91 ± 0.37)% | |
| BC2 | (40.38 ± 0.04)% | (40.86 ± 0.08)% | 38.70% | (57.6 ± 0.27)% | (57.4 ± 1.0)% |
| BC3 | (39.82 ± 0.43)% | (39.33 ± 0.04)% | | (57.85 ± 0.21)% | (54.51 ± 0.30)% |
| BC4 | (32.15 ± 0.12)% | (33.46 ± 0.02)% | 33.61% | (43.17 ± 0.34)% | (43.19 ± 0.16)% |

* Each sample was measured three times, and an average ± SD reported.
** Each sample was measured twice times, and an average ± SD reported.

The invention claimed is:

1. A method to determine the weight percent of an amorphous fraction in an olefin-based polymer composition, comprising one or more olefin-based polymers;
   said method comprising the following steps:
   a) dissolving the olefin-based polymer composition in organic solvent to form a polymer solution;
   b) injecting at least a portion of the polymer solution onto a support material, and wherein the support material comprises one of the following: a) gold particles, b) gold coated particles, c) particles comprising gold, d) particles comprising a coating comprising gold, e) copper particles, f) copper coated particles, g) particles comprising copper, h) particles comprising a coating comprising copper, or i) a combination thereof;
   c) cooling the support material at a rate greater than, or equal to, 0.2° C./min;
   d) increasing the temperature of the support material to elute the polymers of the olefin-based polymer composition;
   e) generating a chromatogram;
   f) determining the peak area of the first elution from its lower integration limit to its upper integration limit;
   g) calculating the amorphous fraction based on the following Equation A below:

$$\text{wt \% amorphous fraction} = PA_{amorp}/PA_{total} \times 100 \quad \text{(Eqn. A)};$$

wherein $PA_{amorp}$=peak area of the first elution, and $PA_{total}$=total peak area of the polymers of the olefin-based polymer composition.

2. The method of claim 1, wherein the olefin-based polymer composition is a block composite ("BC") that comprises the following three polymer components:
   (i) an ethylene-based polymer (EP) having an ethylene content from 10 mol % to less than 90 mol % (a soft copolymer), based on the total moles of polymerized monomer units in the ethylene-based polymer (EP);
   (ii) an alpha-olefin-based polymer (AOP) having an alpha-olefin content of greater than 90 mol % (a hard copolymer), based on the total moles of polymerized monomer units in the alpha-olefin-based polymer (AOP); and
   (iii) a block copolymer having an ethylene block (EB) and an alpha-olefin block (AOB);
   wherein the ethylene block (soft block/soft segment) contains more polymerized ethylene than the alpha-olefin block (hard block/hard segment), and
   wherein the ethylene block has the same or similar Tm as the ethylene-based polymer (EP) of component (i), and
   wherein the alpha-olefin block has the same or similar Tm as the alpha-olefin-based polymer (AOP) of component (ii); and
   wherein the phrase "same or similar" refers to an absolute Tm differential of ≤5° C.

3. The method of claim 1, wherein the olefin-based polymer composition is a crystalline block composite (CBC) that comprises the following three polymer components:
   (i) a crystalline ethylene based polymer (CEP) having an ethylene content of greater than, or equal to, 90 mol % (also referred to herein as a soft polymer of CBC), based on the total moles of polymerized monomer units in the crystalline ethylene-based polymer (CEP);
   (ii) a crystalline alpha-olefin based polymer (CAOP) having an alpha-olefin content of greater than 90 mol % (also referred to herein as a hard polymer of the CBC), based on the total moles of polymerized monomer units in the crystalline alpha-olefin-based polymer (CAOP); and
   (iii) a block copolymer comprising a crystalline ethylene block (CEB) and a crystalline alpha-olefin block (CAOB); and
   wherein the crystalline ethylene block has the same or similar Tm as the crystalline ethylene-based polymer (CEP) of component (i), and
   wherein the crystalline alpha-olefin block has the same or similar Tm as the crystalline alpha-olefin-based polymer (CAOP) of component (ii); and wherein the phrase same or similar refers to an absolute Tm differential of ≤5° C.

4. The method of claim 1, wherein the support material comprises spherical particles that have D50 value less than, or equal to, 100 microns.

5. The method of claim 1, wherein the support material comprises one of the following: a) gold particles, b) gold coated particles, c) particles comprising gold, d) particles comprising a coating comprising gold, e) silver particles, f) silver coated particles, g) particles comprising silver, h) particles comprising a coating comprising silver, or i) a combination thereof.

6. The method of claim 1, wherein the first elution has a lower integration limit from 10° C. to 15° C.

7. The method of claim 1, wherein the first elution has an upper integration limit from 30° ° C. to 45° C., or from 30° ° C. to 40° ° C.

8. The method of claim 1, wherein the first elution is integrated from 10° ° C. to 40° C., or from 12° ° C. to 40° C., or from 15° C. to 40° C.

9. The method of claim 1, wherein the olefin-based polymer composition comprises two olefin-based polymers.

10. The method of claim 1, wherein the olefin-based polymer composition comprises three olefin-based polymers.

11. The method of claim 1, wherein the support material comprises ≥90 wt %, or ≥95 wt %, or ≥98 wt %, or ≥99 wt % of the particles, based on the weight of the support material.

12. The method of claim 1, wherein the olefin-based polymer composition comprises 50 wt %, or a majority amount, of polymerized ethylene, based on the weight of the olefin-based polymer composition.

* * * * *